US009456611B2

(12) United States Patent
Reuveni

(10) Patent No.: US 9,456,611 B2
(45) Date of Patent: Oct. 4, 2016

(54) COMBINATIONS OF ANTIFUNGAL COMPOUNDS AND TEA TREE OIL

(75) Inventor: Moshe Reuveni, Katzrin (IL)

(73) Assignee: STOCKTON (ISRAEL) LTD., Petach Tikva (IL)

(*) Notice: Subject to any disclaimer, the term of this patent is extended or adjusted under 35 U.S.C. 154(b) by 108 days.

(21) Appl. No.: 13/696,081

(22) PCT Filed: May 5, 2011

(86) PCT No.: PCT/US2011/035308
§ 371 (c)(1),
(2), (4) Date: Nov. 28, 2012

(87) PCT Pub. No.: WO2011/140309
PCT Pub. Date: Nov. 10, 2011

(65) Prior Publication Data
US 2013/0064907 A1 Mar. 14, 2013

Related U.S. Application Data

(60) Provisional application No. 61/331,813, filed on May 5, 2010.

(51) Int. Cl.
A61K 36/61 (2006.01)
A01N 65/00 (2009.01)
A01N 65/28 (2009.01)

(52) U.S. Cl.
CPC .............. A01N 65/00 (2013.01); A01N 65/28 (2013.01)

(58) Field of Classification Search
None
See application file for complete search history.

(56) References Cited

U.S. PATENT DOCUMENTS

| 6,022,551 | A | 2/2000 | Jampani et al. |
| 7,910,614 | B2 | 3/2011 | Dietz et al. |
| 7,923,452 | B2 | 4/2011 | Birner et al. |
| 2005/0175714 | A1* | 8/2005 | Pipko et al. ............... 424/717 |
| 2007/0237837 | A1 | 10/2007 | Pipko et al. |
| 2013/0064907 | A1 | 3/2013 | Reuveni |

FOREIGN PATENT DOCUMENTS

| CA | 2647374 A1 | 5/2007 |
| CA | 2769506 A1 | 2/2011 |
| DE | 102005057837 A1 * | 6/2007 |
| EP | 1787652 | 5/2007 |
| JP | H021455502 | 6/1990 |
| JP | 2003095825 A | 4/2003 |
| WO | 9317558 | 9/1993 |
| WO | 9508918 | 4/1995 |
| WO | 9902038 | 1/1999 |
| WO | 9951089 | 10/1999 |
| WO | 2004021792 | 3/2004 |
| WO | 2004037197 | 5/2004 |
| WO | 2006096949 A2 | 9/2006 |
| WO | 2008/035079 | 3/2008 |
| WO | 2008072206 A2 | 6/2008 |
| WO | 2010037089 A1 | 4/2010 |
| WO | 2010037503 | 4/2010 |
| WO | 2010049070 | 5/2010 |

OTHER PUBLICATIONS

FRAC Code List©*: Fungicides sorted by mode of action (including FRAC Code numbering), Fungicide Resistance Action Committee, 2010, pp. 1-10.
Martillo and Reuveni, "A New Potent Bio-Fungicide for the Control of Banana Black Sigatoka", Phytopathology 99:S80 abstract from APS meeting 2009.
Janousek et al. 2009, "Powdery mildew control on pumpkin with organic and synthetic fungicides: 2009 field trial, Department of Plant Pathology UC Davis", available at http://www.escholarship.org/uc/item/8vg8w5pj.
Keith J. Brent and Derek W. Hollomon, "Fungicide Resistance in Crop Pathogens: How Can it Be Managed?", 2nd, revised edition, 2007, Fungicide Resistance Action Committee (FRAC), Croplife International, Avenue Louise 143, 1050 Brussels, Belgium, available online at http://www.frac.info/frac/publication/anhang/FRAC_Mono1_2007_100dpi.pdf.
Reuveni, M., Arroyo, C. J., and . Henriquez, J. L 2009. A new tea tree oil-based organic fungicide for the control of grape powdery and downy mildews. Phytopathology 99:S108 abstract from APS meeting 2009.
Vardi, Y. and Reuveni, M. 2009. Antifungal activity of a new broad spectrum bio-fungicide in the controlling of plant diseases. Phytopathology 99:S134, abstract from APS meeting 2009.
Gary Kemmitt., "Early blight of potato and tomato" downloaded from: http://www.apsnet.org/edcenter/intropp/lessons/fungi/ascomycetes/Pages/PotatoTomato.aspx (2002), updated (2013).

* cited by examiner

Primary Examiner — Chris R Tate
Assistant Examiner — Randall Winston
(74) Attorney, Agent, or Firm — Browdy and Neimark, PLLC

(57) ABSTRACT

There is disclosed a method for treating a plant infection caused by a fungus of the class ascomycetes, comprising applying to the plant a combination of tea tree oil (TTO) and a synthetic fungicidal compound. Other embodiments are also disclosed.

15 Claims, 5 Drawing Sheets

COMBINATIONS OF ANTIFUNGAL COMPOUNDS AND TEA TREE OIL

Figure 1A:
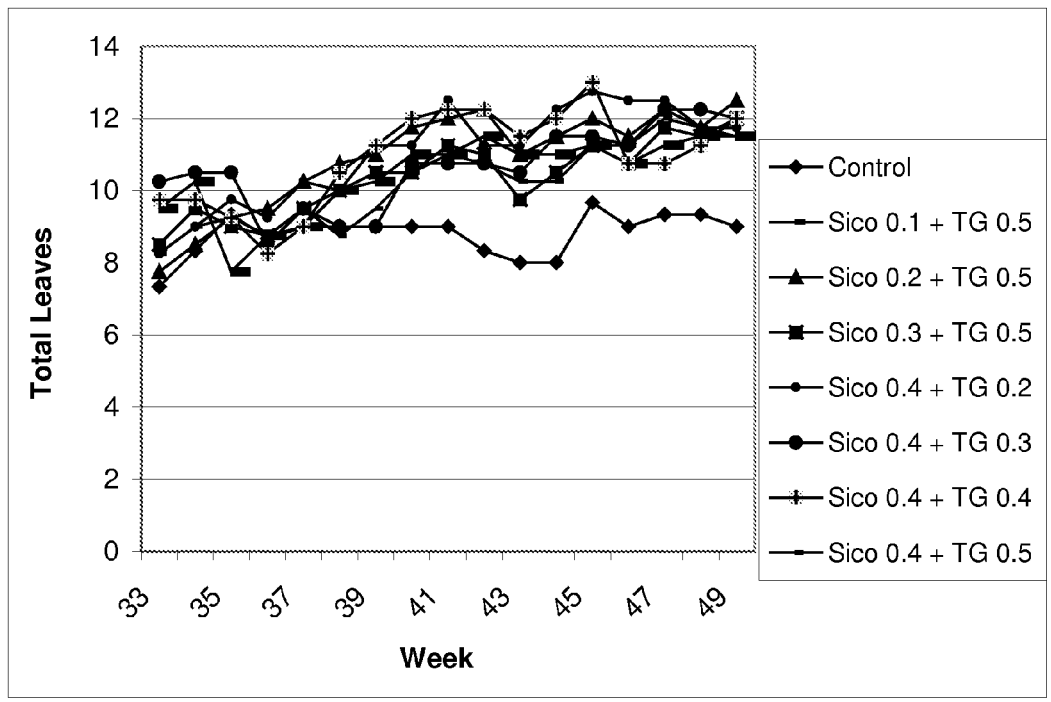

This application claims the benefit of U.S. Provisional Application No. 61/331,813, entitled "Combinations of Antifungal Compounds and TTO-Containing Compositions", filed May 5, 2010, the contents of which are incorporated herein by reference.

BACKGROUND

Infection of crops by fungi is a well-documented problem that can significantly affect crop yields. Various treatments of fungi by synthetic (chemical) products (including both curative and prophylactic treatments) have been developed, but they present problems as well. One problem, for example, is the effect of the so-called chemical load on the environment, animal and human health, and food safety. For these and other reasons, the popularity of "organic" or "bio-" fungicides, i.e. those derived from natural sources, has increased in recent years.

An additional problem encountered with the use of synthetic antifungal compounds, noticed by the early 1970's, is that resistance to such antifungal compounds sometimes develops. For example, the classes of antifungal compounds known as DMIs and strobilurins (discussed below) are biochemically active on a specific target site, and their broad use has led to fungal strains becoming less sensitive to other members of these classes of compounds. In response, various methods for countering such resistance when it occurs, or for reducing the likelihood of such resistance even developing, have been developed to enable continued use of synthetic fungicidal compounds when possible. These methods, also called "resistance management strategies", include, among other steps, the simultaneous or sequential use of combinations of synthetic antifungal compounds that have different modes of action, limiting the number of uses of a particular antifungal compound during a giving growing season, and applying a given antifungal at a dosage that equals or exceed a particular minimum dosage. See, e.g. Keith J. Brent and Derek W. Hollomon, "Fungicide Resistance in Crop Pathogens: How Can it Be Managed?", $2^{nd}$ revised edition, 2007, Fungicide Resistance Action Committee (FRAC), Croplife International, Avenue Louise 143, 1050 Brussels, Belgium, available online at http://www.frac.info/frac/publication/anhang/FRAC_Mono1_2007_100 dpi.pdf.

In addition to combining fungicides in order to delay or reduce the emergence of resistant strains, fungicides are also often combined in mixtures in order to widen the spectrum and extend the duration of antifungal activity; and to exploit synergistic interaction between the active fungicidal compounds, whereby the overall activity can be increased. Synergy, which is a frequent phenomenon in fungicide mixtures, may occur between antifungal compounds of different natures and sources, between fungicides with different or identical modes of action, and between those prepared in different formulations.

While in principle combinations of synthetic antifungal compounds could be used to reduce the chemical load of any particular synthetic antifungal compound applied to crops, the fear of resistance at such lower loads has mitigated against the use of such lower loads, as reflected in the FRAC paper referenced above.

In the case of bananas in particular, infection by *Mycosphaerella fijensis*, a fungus of the class ascomycetes, commonly known as Black Sigatoka, is a well-known and widespread problem. Currently, chemical treatment of Black Sigatoka is effected using one or a mixture of synthetic fungicidal compounds, which can be categorized into five major groups (although some fungicidal compounds used do not fall into one of these groups): (a) demethylation inhibitors (DMIs), (b) Amines, (c) Quinone outside Inhibitors (QoIs), (d) Anilinopyrimidines (APs), and (e) Benzimidazoles. According to the web page of the FRAC Banana Working Group on the FRAC website (http://www.frac.info/frac/index.htm), (i) the DMI fungicides presently used in banana cropping are bitertanol, difenoconazole, epoxiconazole, fenbuconazole, flusilazole, hexaconazole, myclobutanil, propiconazole, tebuconazole, tetraconazole and triadimenol (all of these compounds are triazoles); (ii) the amine fungicides presently used in banana cropping are spiroxamine, fenpropimorph and tridemorph; (iii) the QoI fungicides presently used in banana cropping are azoxystrobin, pyraclostrobin and trifloxystrobin (all which are belong to a class of molecules sometimes called strobilurins); (iv) pyrimethanil is the only active ingredient from the group of anilinopyrimidines currently used in banana cropping; and (v) the benzimidazoles presently used in banana cropping are benomyl, carbendazim, thiabendazole, thiophanate and thiophanate-methyl (although the latter two area actually thiophanates rather than benzimidazoles, but they are classed by FRAC with the benzimidazoles). These compounds are applied to the leaves of banana plants—the part of the plant where Black Sigatoka infections occur—by spraying a composition containing one or more of the compounds listed above as the active ingredient(s). Some dithiocarbamates (e.g. mancozeb) and spiroxamines (spiroxamine) are also used to treat Black Sigatoka.

The FRAC Banana Working Group sets out the following guidelines for all fungicides used to treat bananas: (a) for a combination of active ingredients to be effective in a resistance management strategy, the rate of application of each active ingredient must be sufficient to provide satisfactory control when used alone at the same rate; (b) the recommended label rate of each mixture component must be respected; (c) protectant (multi-site) fungicides are considered to be a very valuable and necessary tool for the banana Sigatoka control programs and resistance management; and (d) site-specific fungicides must be applied in oil or oil-water emulsions. Guidelines (a) and (b), alone and in combination, mean that banana growers do not reduce the dosages of fungicides, even when from a short-term economic and an environmental standpoint it would be desirable to do so, e.g. to reduce expenditures on fungicides or to reduce chemical run-off into the ground.

Similarly, other crop diseases caused by fungi of the class ascomycetes may be treated using synthetic fungicidal compounds, but here too the development of resistance is a concern. Emulsions containing tea tree oil (TTO) for fungicidal application to plants, e.g. to plant leaves, are known. See, for example, US Patent Publication No. 2007/0237837, and the commercial product available under the name Timorex Gold from Biomor Israel Ltd., P.O. Box 81, Qatzrin 12900 Israel, http://www.biomor.com/timorex%20gold.htm. Timorex Gold has been successfully applied to combat Black Sigatoka (see e.g. Eduardo and Reuveni, "A New Potent Bio-Fungicide For the Control of Banana Black Sigatoka", *Phytopathology* 2009, abstract from APS meeting 2009), although neither TTO in general nor Timorex Gold in particular appear in the FRAC Banana Working Group's list of fungicides used to treat Black Sigatoka. Similarly, Timorex Gold has been used alone to combat ascomycetes fungi in other crops.

BRIEF DESCRIPTION OF EMBODIMENTS OF THE INVENTION

There is provided in accordance with an embodiment of the invention a method for treating a plant infection caused by a fungus of the class ascomycetes, comprising applying to the plant a combination of tea tree oil (TTO) and a synthetic fungicidal compound. In some embodiments, the infection is caused by a fungus selected from the group consisting of Erysiphales, Dothiodoales, Pleosporales, Capnodiales and Magnoporthales. In some embodiments, the infection is selected from the group consisting of banana plant Black Sigatoka, carrot *alternaria*, tomato powdery mildew, and pepper powdery mildew. In some embodiments, the combination is applied to the leaves of the plant.

In some embodiments, the TTO is applied as a TTO-containing composition. In some embodiments, the TTO-containing composition comprises TTO and an emulsifier. In some embodiments the emulsifier is an alkali or ammonium salt of a $C_6$-$C_{26}$ fatty acid or a mixture of such salts. In some embodiments the emulsifier is selected from the group consisting of ethoxylated fatty acids, ethoxylated castor oils, ethoxylated polyglycol ethers, alkoxylates, sorbitan esters, dodecylbenzene sulphonates, and ethoxylated tristyrylphenol phosphates. In some embodiments, the TTO-containing composition is an oil-in-water emulsion. In some embodiments, the TTO is present in the TTO-containing composition in an amount of from 0.01 wt. % to 10 wt. %. In some embodiments, the TTO is present in the TTO-containing composition in an amount of not more than 9 wt. %. In some embodiments, the TTO is present in the TTO-containing composition in an amount of not more than 8 wt. %. In some embodiments, the TTO is present in the TTO-containing composition in an amount of not more than 7 wt. %. In some embodiments, the TTO is present in the TTO-containing composition in an amount of not more than 6 wt. %. In some embodiments, the TTO is present in the TTO-containing composition in an amount of not more than 5 wt. %. In some embodiments, the TTO is present in the TTO-containing composition in an amount of not more than 4 wt. %. In some embodiments, the TTO is present in the TTO-containing composition in an amount of not more than 3 wt. %. In some embodiments, the TTO is present in the TTO-containing composition in an amount of not more than 2 wt. %. In some embodiments, the TTO is present in the TTO-containing composition in an amount of not more than 1 wt. %. In some embodiments, the TTO is present in the TTO-containing composition in an amount of at least 0.02 wt. %. In some embodiments, the TTO is present in the TTO-containing composition in an amount of at least 0.03 wt. %. In some embodiments, the TTO is present in the TTO-containing composition in an amount of at least 0.04 wt. %. In some embodiments, the TTO is present in the TTO-containing composition in an amount of at least 0.05 wt. %. In some embodiments, the TTO is present in the TTO-containing composition in an amount of at least 0.06 wt. %. In some embodiments, the TTO is present in the TTO-containing composition in an amount of at least 0.07 wt. %. In some embodiments, the TTO is present in the TTO-containing composition in an amount of at least 0.08 wt. %. In some embodiments, the TTO is present in the TTO-containing composition in an amount of at least 0.09 wt. %. In some embodiments, the TTO is present in the TTO-containing composition in an amount of at least 0.1 wt. %. In some embodiments, the TTO is present in the TTO-containing composition in an amount of at least 0.2 wt. %. In some embodiments, the TTO is present in the TTO-containing composition in an amount of at least 0.3 wt. %. In some embodiments, the TTO is present in the TTO-containing composition in an amount of at least 0.4 wt. %. In some embodiments, the TTO is present in the TTO-containing composition in an amount of at least 0.5 wt. %. In some embodiments, the TTO is present in the TTO-containing composition in an amount of at least 0.6 wt. %. In some embodiments, the TTO is present in the TTO-containing composition in an amount of at least 0.7 wt. %. In some embodiments, the TTO is present in the TTO-containing composition in an amount of at least 0.8 wt. %. In some embodiments, the TTO is present in the TTO-containing composition in an amount of at least 0.9 wt. %. In some embodiments, the TTO is present in the TTO-containing composition in an amount of at least 1.0 wt. %.

In some embodiments, the TTO-containing composition further comprises an additional etheric oil. In some embodiments, the additional etheric oil is selected from the group consisting of lavender (*Lavandula angustifolia*) oil, pine (*Pinus sylvestris*) oil, manuka (*Leptosperemum scoparium*) oil, kanuca (*Kunzea ericoids*) oil, eucalyptus (*Eucaluptus globules*) oil, bergamot (*Citrus bergamia*) oil, clove (*Eugenia caryaphylata*) oil, lemon (*Citrus limoneum*) oil, lemon grass (*Cymbpogon citrates*) oil, rosemary (*Rosmarinus officialis*) oil, geranium (*Pelargonium graveoleus*) oil, and mint oil, the latter of which refers to an etheric oil containing high levels of menthol and/or methane; and mixtures thereof.

In some embodiments, the TTO-containing composition further comprises the synthetic fungicidal compound. In some embodiments, the combination of TTO and synthetic fungicidal compound is applied simultaneously. In some embodiments, the combination of TTO and synthetic fungicidal compound is applied as a single mixture. In some embodiments, the combination of TTO and synthetic fungicidal compound is applied sequentially. In some embodiments, the combination of TTO and synthetic fungicidal compound is applied as separate compositions. In some embodiments, the combination of TTO and synthetic fungicidal compound is applied in conjunction with at least one of a mineral oil and an emulsifier.

In some embodiments, the synthetic fungicidal compound is applied at a dosage rate that is less than the rate indicated by the manufacturer as being the correct dosage rate in the absence of TTO. In some embodiments, the dosage rate at which the synthetic fungicidal compound is applied is not greater than 95% of the correct dosage rate as indicated by the manufacturer in the absence of TTO. In some embodiments, the dosage rate at which the synthetic fungicidal compound is applied is not greater than 90% of the correct dosage rate as indicated by the manufacturer in the absence of TTO. In some embodiments, the dosage rate at which the synthetic fungicidal compound is applied is not greater than 85% of the correct dosage rate as indicated by the manufacturer in the absence of TTO. In some embodiments, the dosage rate at which the synthetic fungicidal compound is applied is not greater than 80% of the correct dosage rate as indicated by the manufacturer in the absence of TTO. In some embodiments, the dosage rate at which the synthetic fungicidal compound is applied is not greater than 75% of the correct dosage rate as indicated by the manufacturer in the absence of TTO. In some embodiments, the dosage rate at which the synthetic fungicidal compound is applied is not greater than 70% of the correct dosage rate as indicated by the manufacturer in the absence of TTO. In some embodiments, the dosage rate at which the synthetic fungicidal compound is applied is not greater than 65% of the correct dosage rate as indicated by the manufacturer in the absence of TTO. In some embodiments, the dosage rate at which the synthetic fungicidal compound is applied is not greater than 60% of the correct dosage rate as indicated by the manufacturer in the absence of TTO. In some embodiments, the dosage rate at which the synthetic fungicidal compound is applied is not greater than 55% of the correct dosage rate as indicated by the manufacturer in the absence of TTO. In some embodiments, the dosage rate at which the synthetic fungicidal compound is applied is not greater than 50% of the correct dosage rate as indicated by the manufacturer in the absence of TTO. In some embodiments, the dosage rate at which the synthetic fungicidal compound is applied is not greater than 45% of the correct dosage rate as indicated by the manufacturer in the absence of TTO. In some embodiments, the dosage rate at which the synthetic fungicidal compound is applied is not greater than 40% of the correct dosage rate as indicated by the manufacturer in the absence of TTO. In some embodiments, the dosage rate at which the synthetic fungicidal compound is applied is not greater than 35% of the correct dosage rate as indicated by the manufacturer in the absence of TTO. In some embodiments, the dosage rate at which the synthetic fungicidal compound is applied is not greater than 30% of the correct dosage rate as indicated by the manufacturer in the absence of TTO. In some embodiments, the dosage rate at which the synthetic fungicidal compound is applied is at least 40% of the correct dosage rate as indicated by the manufacturer in the absence of TTO. In some embodiments, the dosage rate at which the synthetic fungicidal compound is applied is at least 45% of the correct dosage rate as indicated by the manufacturer in the absence of TTO. In some embodiments, the dosage rate at which the synthetic fungicidal compound is applied is at least 50% of the correct dosage rate as indicated by the manufacturer in the absence of TTO. In some embodiments, the dosage rate at which the synthetic fungicidal compound is applied is at least 55% of the correct dosage rate as indicated by the manufacturer in the absence of TTO. In some embodiments, the dosage rate at which the synthetic fungicidal compound is applied is at least 60% of the correct dosage rate as indicated by the manufacturer in the absence of TTO. In some embodiments, the dosage rate at which the synthetic fungicidal compound is applied is at least 65% of the correct dosage rate as indicated by the manufacturer in the absence of TTO. In some embodiments, the dosage rate at which the synthetic fungicidal compound is applied is at least 70% of the correct dosage rate as indicated by the manufacturer in the absence of TTO. In some embodiments, the dosage rate at which the synthetic fungicidal compound is applied is at least 75% of the correct dosage rate as indicated by the manufacturer in the absence of TTO.

In some embodiments, the TTO is applied at a dosage rate that is less than the rate indicated by the manufacturer as the rate used when the TTO is applied in the absence of a synthetic fungicidal compound. In some embodiments, the dosage rate at which the TTO is applied is not greater than 95% of the correct dosage rate as indicated by the manufacturer in the absence of application of a synthetic fungicidal compound. In some embodiments, the dosage rate at which the TTO is applied is not greater than 90% of the correct dosage rate as indicated by the manufacturer in the absence of application of a synthetic fungicidal compound. In some embodiments, the dosage rate at which the TTO is applied is not greater than 85% of the correct dosage rate as indicated by the manufacturer in the absence of application of a synthetic fungicidal compound. In some embodiments, the dosage rate at which the TTO is applied is not greater than 80% of the correct dosage rate as indicated by the manufacturer in the absence of application of a synthetic fungicidal compound. In some embodiments, the dosage rate at which the TTO is applied is not greater than 75% of the correct dosage rate as indicated by the manufacturer in the absence of application of a synthetic fungicidal compound. In some embodiments, the dosage rate at which the TTO is applied is not greater than 70% of the correct dosage rate as indicated by the manufacturer in the absence of application of a synthetic fungicidal compound. In some embodiments, the dosage rate at which the TTO is applied is not greater than 65% of the correct dosage rate as indicated by the manufacturer in the absence of application of a synthetic fungicidal compound. In some embodiments, the dosage rate at which the TTO is applied is not greater than 60% of the correct dosage rate as indicated by the manufacturer in the absence of application of a synthetic fungicidal compound. In some embodiments, the dosage rate at which the TTO is applied is not greater than 55% of the correct dosage rate as indicated by the manufacturer in the absence of application of a synthetic fungicidal compound. In some embodiments, the dosage rate at which the TTO is applied is not greater than 50% of the correct dosage rate as indicated by the manufacturer in the absence of application of a synthetic fungicidal compound. In some embodiments, the dosage rate at which the TTO is applied is not greater than 45% of the correct dosage rate as indicated by the manufacturer in the absence of application of a synthetic fungicidal compound. In some embodiments, the dosage rate at which the TTO is applied is not greater than 40% of the correct dosage rate as indicated by the manufacturer in the absence of application of a synthetic fungicidal compound. In some embodiments, the TTO is applied is not greater than 35% of the correct dosage rate as indicated by the manufacturer in the absence of application of a synthetic fungicidal compound. In some embodiments, the dosage rate at which the TTO is applied is not greater than 30% of the correct dosage rate as indicated by the manufacturer in the absence of application of a synthetic fungicidal compound. In some embodiments, the dosage rate at which the TTO is applied is at least 40% of the correct dosage rate as indicated by the manufacturer in the absence of application of a synthetic fungicidal compound. In some embodiments, the dosage rate at which the TTO is applied is at least 45% of the correct dosage rate as indicated by the manufacturer in the absence of application of a synthetic fungicidal compound. In some embodiments, the dosage rate at which the TTO is applied is at least 50% of the correct dosage rate as indicated by the manufacturer in the absence of application of a synthetic fungicidal compound. In some embodiments, the dosage rate at which the TTO is applied is at least 55% of the correct dosage rate as indicated by the manufacturer in the absence of application of a synthetic fungicidal compound. In some embodiments, the dosage rate at which the TTO is applied is at least 60% of the correct dosage rate as indicated by the manufacturer in the absence of application of a synthetic fungicidal compound. In some embodiments, the dosage rate at which the TTO is applied is at least 65% of the correct dosage rate as indicated by the manufacturer in the absence of application of a synthetic fungicidal compound. In some embodiments, the dosage rate at which the TTO is applied is at least 70% of the correct dosage rate as indicated by the manufacturer in the absence of application of a synthetic fungicidal compound. In some embodiments, the dosage rate at which the TTO composition is applied is at least 75% of the correct dosage rate as indicated by the manufacturer in the absence of application of a synthetic fungicidal compound.

In some embodiments, the synthetic fungicidal compound is selected from the group consisting of demethylation inhibitors (DMIs), Amines, Quinone outside Inhibitors (QoIs), Anilinopyrimidines (APs), and Benzimidazoles, Carboxamides and Morpholines.

In some embodiments, the synthetic fungicidal compound is a fungicidal compound indicated for the treatment of Black Sigatoka which is selected from the group consisting of demethylation inhibitors (DMIs), Amines, Quinone outside Inhibitors (QoIs), Anilinopyrimidines (APs), and Benzimidazoles, as presently defined by the Fungicide Resistance Action Committee (FRAC) Banana Group, and the combination is applied to at least one banana plant. In some embodiments, the fungicidal compound is a demethylation inhibitor (DMI) selected from the group consisting of bitertanol, difenoconazole, epoxiconazole, fenbuconazole, flusilazole, hexaconazole, myclobutanil, propiconazole, tebuconazole, tetraconazole and triadimenol. In some embodiments, the fungicidal compound is a DMI other than bitertanol, difenoconazole, epoxiconazole, fenbuconazole, flusilazole, hexaconazole, myclobutanil, propiconazole, tebuconazole, tetraconazole and triadimenol. In some embodiments, the DMI is selected from imazalil, fenarimol and flutriafol. In some embodiments, the synthetic fungicidal compound is an amine fungicidal compound selected from the group consisting of spiroxamine, fenpropimorph and tridemorph. In some embodiments, the synthetic fungicidal compound is a QoI fungicidal compound selected from the group consisting of azoxystrobin, pyraclostrobin, kesoxym-methyl, picoxystrobin, pyrmetostrobin and trifloxystrobin. In some embodiments, the synthetic fungicidal compound is a strobilurin other than azoxystrobin, pyraclostrobin, kesoxym-methyl, picoxystrobin, pyrmetostrobin and trifloxystrobin.

In some embodiments, the synthetic fungicidal compound is pyrimethanil. In some embodiments, the synthetic fungicidal compound is a benzimidazole selected from the group consisting of benomyl, carbendazim, thiabendazole, thiophanate and thiophanate-methyl.

In some embodiments, the synthetic fungicidal compound is a fungicidal compound indicated for the treatment of Black Sigatoka which is selected from the group consisting of mancozeb, chlorothalonil, boscalid and dodine.

In some embodiments, the synthetic fungicidal compound is a compound that is indicated for the treatment of tomato powdery mildew or pepper powdery mildew, and the combination is applied to at least one tomato or pepper plant. In some embodiments, the synthetic fungicidal compound is selected from the group consisting of azoxystrobin, trifloxystrobin, myclobutanil, and triadimenol.

In some embodiments, the synthetic fungicidal compound is indicated for the treatment of carrot *alternaria* and the combination is applied to at least one carrot plant. In some embodiments, the synthetic fungicidal compound is difenoconazole.

In some embodiments, the synthetic fungicidal compound is selected from the group consisting of mancozeb, chlorothalonil, trifloxystrobin, krsoxim-methyl, orysastrobin, fluoxastrobin, azoxystrobin, pyraclostrobin, dimoxystrobin, picoxystrobin, carbendazim, thiophanate-methyl, thiophanate, thiabendazole, benomyl, boscalid, penthiopyrad, thifluzamide, bixafen, fluopyram, isopyrazam, fenpropimorph, fenpropidin, fenarimol, triforine, spiroxamine, tridemorph, elemental sulfur, quinoxyfen, meptyl dinocap, bupirimate, proquinazid, metrafenone, cyflufenamid, tebuconazole, epoxiconazole, propiconazole, prothioconazole, cyproconazole, difenoconazole, metconazole, flusilazole, myclobutanil, flutriafol, triadimefon, penconazole, bitertanol, hexaconazole, triadimenol, tetraconazole, fluquinconazole, triticonazole, fenbuconazole, diniconazole, bromuconazole, ipconazole, simeconazole, imibenconazole, azaconazole, etaconazole and diclobutrazol.

In some embodiments, the treatment is prophylactic treatment. In some embodiments, the treatment is curative.

There are also provided, in accordance with embodiments of the invention, (1) a method for reducing the dosage rate of a synthetic compound that has fungicidal activity against a plant-infection causing fungus of the class ascomycetes, comprising applying to a plant having such an infection which has been treated with such a synthetic fungicidal compound a tea tree oil (TTO)-containing composition; and (2) a method for reducing the dosage rate of a TTO-containing composition, comprising applying to a plant having an infection caused by a fungus of the class ascomycetes which has been treated with a TTO-containing composition a synthetic fungicidal compound.

In some embodiments, the infection is caused by a fungus selected from the group consisting of Erysiphales, Dothiodoales, Pleosporales, Capnodiales and Magnoporthales. In some embodiments, the infection is selected from the group consisting of banana plant Black Sigatoka, carrot *alternaria*, tomato powdery mildew, and pepper powdery mildew. In some embodiments, the composition is applied to the leaves of the plant.

In some embodiments, the TTO-containing composition comprises TTO and an emulsifier. In some embodiments the emulsifier is an alkali or ammonium salt of a $C_6$-$C_{26}$ fatty acid or a mixture of such salts. In some embodiments the emulsifier is selected from the group consisting of ethoxylated fatty acids, ethoxylated castor oils, ethoxylated polyglycol ethers, alkoxylates, sorbitan esters, dodecylbenzene sulphonates, and ethoxylated tristyrylphenol phosphates. In some embodiments, the TTO-containing composition is an oil-in-water emulsion. In some embodiments, the TTO is present in the TTO-containing composition in an amount of from 0.01 wt. % to 10 wt. %. In some embodiments, the TTO is present in the TTO-containing composition in an amount of not more than 9 wt. %. In some embodiments, the TTO is present in the TTO-containing composition in an amount of not more than 8 wt. %. In some embodiments, the TTO is present in the TTO-containing composition in an amount of not more than 7 wt. %. In some embodiments, the TTO is present in the TTO-containing composition in an amount of not more than 6 wt. %. In some embodiments, the TTO is present in the TTO-containing composition in an amount of not more than 5 wt. %. In some embodiments, the TTO is present in the TTO-containing composition in an amount of not more than 4 wt. %. In some embodiments, the TTO is present in the TTO-containing composition in an amount of not more than 3 wt. %. In some embodiments, the TTO is present in the TTO-containing composition in an amount of not more than 2 wt. %. In some embodiments, the TTO is present in the TTO-containing composition in an amount of not more than 1 wt. %. In some embodiments, the TTO is present in the TTO-containing composition in an amount of at least 0.02 wt. %. In some embodiments, the TTO is present in the TTO-containing composition in an amount of at least 0.03 wt. %. In some embodiments, the TTO is present in the TTO-containing composition in an amount of at least 0.04 wt. %. In some embodiments, the TTO is present in the TTO-containing composition in an amount of at least 0.05 wt. %. In some embodiments, the TTO is present in the TTO-containing composition in an amount of at least 0.06 wt. %. In some embodiments, the TTO is present in the TTO-containing composition in an amount of at least 0.07 wt. %. In some embodiments, the TTO is present in the TTO-containing composition in an amount of at least 0.08 wt. %. In some embodiments, the TTO is present in the TTO-containing composition in an amount of at least 0.09 wt. %. In some embodiments, the TTO is present in the TTO-containing composition in an amount of at least 0.1 wt. %. In some embodiments, the TTO is present in the TTO-containing composition in an amount of at least 0.2 wt. %. In some embodiments, the TTO is present in the TTO-containing composition in an amount of at least 0.3 wt. %. In some embodiments, the TTO is present in the TTO-containing composition in an amount of at least 0.4 wt. %. In some embodiments, the TTO is present in the TTO-containing composition in an amount of at least 0.5 wt. %. In some embodiments, the TTO is present in the TTO-containing composition in an amount of at least 0.6 wt. %. In some embodiments, the TTO is present in the TTO-containing composition in an amount of at least 0.7 wt. %. In some embodiments, the TTO is present in the TTO-containing composition in an amount of at least 0.8 wt. %. In some embodiments, the TTO is present in the TTO-containing composition in an amount of at least 0.9 wt. %. In some embodiments, the TTO is present in the TTO-containing composition in an amount of at least 1.0 wt. %.

In some embodiments, the TTO-containing composition further comprises an additional etheric oil. In some embodiments, the additional etheric oil is selected from the group consisting of lavender (*Lavandula angustifolia*) oil, pine (*Pinus sylvestris*) oil, manuka (*Leptosperemum scoparium*) oil, kanuca (*Kunzea ericoids*) oil, eucalyptus (*Eucaluptus globules*) oil, bergamot (*Citrus bergamia*) oil, clove (*Eugenia caryaphylata*) oil, lemon (*Citrus limoneum*) oil, lemon grass (*Cymbpogon citrates*) oil, rosemary (*Rosmarinus officialis*) oil, geranium (*Pelargonium graveoleus*) oil, and mint oil, the latter of which refers to an etheric oil containing high levels of menthol and/or methane; and mixtures thereof.

In some embodiments, the TTO-containing composition further comprises the synthetic fungicidal compound. In some embodiments, the combination of TTO and synthetic fungicidal compound is applied simultaneously. In some embodiments, the combination of TTO and synthetic fungicidal compound is applied as a single mixture. In some embodiments, the combination of TTO and synthetic fungicidal compound is applied sequentially. In some embodiments, the combination of TTO and synthetic fungicidal compound is applied as separate compositions. In some embodiments, the combination of TTO and synthetic fungicidal compound is applied in conjunction with at least one of a mineral oil and an emulsifier.

In some embodiments, the synthetic fungicidal compound is applied at a dosage rate that is less than the rate indicated by the manufacturer as being the correct dosage rate in the absence of TTO. In some embodiments, the dosage rate at which the synthetic fungicidal compound is applied is not greater than 95% of the correct dosage rate as indicated by the manufacturer in the absence of TTO. In some embodiments, the dosage rate at which the synthetic fungicidal compound is applied is not greater than 90% of the correct dosage rate as indicated by the manufacturer in the absence of TTO. In some embodiments, the dosage rate at which the synthetic fungicidal compound is applied is not greater than 85% of the correct dosage rate as indicated by the manufacturer in the absence of TTO. In some embodiments, the dosage rate at which the synthetic fungicidal compound is applied is not greater than 80% of the correct dosage rate as indicated by the manufacturer in the absence of TTO. In some embodiments, the dosage rate at which the synthetic fungicidal compound is applied is not greater than 75% of the correct dosage rate as indicated by the manufacturer in the absence of TTO. In some embodiments, the dosage rate at which the synthetic fungicidal compound is applied is not greater than 70% of the correct dosage rate as indicated by the manufacturer in the absence of TTO. In some embodiments, the dosage rate at which the synthetic fungicidal compound is applied is not greater than 65% of the correct dosage rate as indicated by the manufacturer in the absence of TTO. In some embodiments, the dosage rate at which the synthetic fungicidal compound is applied is not greater than 60% of the correct dosage rate as indicated by the manufacturer in the absence of TTO. In some embodiments, the dosage rate at which the synthetic fungicidal compound is applied is not greater than 55% of the correct dosage rate as indicated by the manufacturer in the absence of TTO. In some embodiments, the dosage rate at which the synthetic fungicidal compound is applied is not greater than 50% of the correct dosage rate as indicated by the manufacturer in the absence of TTO. In some embodiments, the dosage rate at which the synthetic fungicidal compound is applied is not greater than 45% of the correct dosage rate as indicated by the manufacturer in the absence of TTO. In some embodiments, the dosage rate at which the synthetic fungicidal compound is applied is not greater than 40% of the correct dosage rate as indicated by the manufacturer in the absence of TTO. In some embodiments, the dosage rate at which the synthetic fungicidal compound is applied is not greater than 35% of the correct dosage rate as indicated by the manufacturer in the absence of TTO. In some embodiments, the dosage rate at which the synthetic fungicidal compound is applied is not greater than 30% of the correct dosage rate as indicated by the manufacturer in the absence of TTO. In some embodiments, the dosage rate at which the synthetic fungicidal compound is applied is at least 40% of the correct dosage rate as indicated by the manufacturer in the absence of TTO. In some embodiments, the dosage rate at which the synthetic fungicidal compound is applied is at least 45% of the correct dosage rate as indicated by the manufacturer in the absence of TTO. In some embodiments, the dosage rate at which the synthetic fungicidal compound is applied is at least 50% of the correct dosage rate as indicated by the manufacturer in the absence of TTO. In some embodiments, the dosage rate at which the synthetic fungicidal compound is applied is at least 55% of the correct dosage rate as indicated by the manufacturer in the absence of TTO. In some embodiments, the dosage rate at which the synthetic fungicidal compound is applied is at least 60% of the correct dosage rate as indicated by the manufacturer in the absence of TTO. In some embodiments, the dosage rate at which the synthetic fungicidal compound is applied is at least 65% of the correct dosage rate as indicated by the manufacturer in the absence of TTO. In some embodiments, the dosage rate at which the synthetic fungicidal compound is applied is at least 70% of the correct dosage rate as indicated by the manufacturer in the absence of TTO. In some embodiments, the dosage rate at which the synthetic fungicidal compound is applied is at least 75% of the correct dosage rate as indicated by the manufacturer in the absence of TTO.

In some embodiments, the TTO-containing composition is applied at a dosage rate that is less than the rate indicated by the manufacturer as the rate used when the TTO-containing composition is applied in the absence of a synthetic fungicidal compound. In some embodiments, the dosage rate at which the TTO-containing composition is applied is not greater than 95% of the correct dosage rate as indicated by the manufacturer in the absence of application of a synthetic fungicidal compound. In some embodiments, the dosage rate at which the TTO-containing composition is applied is not greater than 90% of the correct dosage rate as indicated by the manufacturer in the absence of application of a synthetic fungicidal compound. In some embodiments, the dosage rate at which the TTO-containing composition is applied is not greater than 85% of the correct dosage rate as indicated by the manufacturer in the absence of application of a synthetic fungicidal compound. In some embodiments, the dosage rate at which the TTO-containing composition is applied is not greater than 80% of the correct dosage rate as indicated by the manufacturer in the absence of application of a synthetic fungicidal compound. In some embodiments, the dosage rate at which the TTO-containing composition is applied is not greater than 75% of the correct dosage rate as indicated by the manufacturer in the absence of application of a synthetic fungicidal compound. In some embodiments, the dosage rate at which the TTO-containing composition is applied is not greater than 70% of the correct dosage rate as indicated by the manufacturer in the absence of application of a synthetic fungicidal compound. In some embodiments, the dosage rate at which the TTO-containing composition is applied is not greater than 65% of the correct dosage rate as indicated by the manufacturer in the absence of application of a synthetic fungicidal compound. In some embodiments, the dosage rate at which the TTO-containing composition is applied is not greater than 60% of the correct dosage rate as indicated by the manufacturer in the absence of application of a synthetic fungicidal compound. In some embodiments, the dosage rate at which the TTO-containing composition is applied is not greater than 55% of the correct dosage rate as indicated by the manufacturer in the absence of application of a synthetic fungicidal compound. In some embodiments, the dosage rate at which the TTO-containing composition is applied is not greater than 50% of the correct dosage rate as indicated by the manufacturer in the absence of application of a synthetic fungicidal compound. In some embodiments, the dosage rate at which the TTO-containing composition is applied is not greater than 45% of the correct dosage rate as indicated by the manufacturer in the absence of application of a synthetic fungicidal compound. In some embodiments, the dosage rate at which the TTO-containing composition is applied is not greater than 40% of the correct dosage rate as indicated by the manufacturer in the absence of application of a synthetic fungicidal compound. In some embodiments, the TTO-containing composition is applied is not greater than 35% of the correct dosage rate as indicated by the manufacturer in the absence of application of a synthetic fungicidal compound. In some embodiments, the dosage rate at which the TTO-containing composition is applied is not greater than 30% of the correct dosage rate as indicated by the manufacturer in the absence of application of a synthetic fungicidal compound. In some embodiments, the dosage rate at which the TTO-containing composition is applied is at least 40% of the correct dosage rate as indicated by the manufacturer in the absence of application of a synthetic fungicidal compound. In some embodiments, the dosage rate at which the TTO-containing composition is applied is at least 45% of the correct dosage rate as indicated by the manufacturer in the absence of application of a synthetic fungicidal compound. In some embodiments, the dosage rate at which the TTO-containing composition is applied is at least 50% of the correct dosage rate as indicated by the manufacturer in the absence of application of a synthetic fungicidal compound. In some embodiments, the dosage rate at which the TTO-containing composition is applied is at least 55% of the correct dosage rate as indicated by the manufacturer in the absence of application of a synthetic fungicidal compound. In some embodiments, the dosage rate at which the TTO-containing composition is applied is at least 60% of the correct dosage rate as indicated by the manufacturer in the absence of application of a synthetic fungicidal compound. In some embodiments, the dosage rate at which the TTO-containing composition is applied is at least 65% of the correct dosage rate as indicated by the manufacturer in the absence of application of a synthetic fungicidal compound. In some embodiments, the dosage rate at which the TTO-containing composition is applied is at least 70% of the correct dosage rate as indicated by the manufacturer in the absence of application of a synthetic fungicidal compound. In some embodiments, the dosage rate at which the TTO-containing composition is applied is at least 75% of the correct dosage rate as indicated by the manufacturer in the absence of application of a synthetic fungicidal compound.

In some embodiments, the synthetic fungicidal compound is selected from the group consisting of demethylation inhibitors (DMIs), Amines, Quinone outside Inhibitors (QoIs), Anilinopyrimidines (APs), Benzimidazoles, Carboxamides and Morpholines.

In some embodiments, the synthetic fungicidal compound is a fungicidal compound indicated for the treatment of Black Sigatoka which is selected from the group consisting of demethylation inhibitors (DMIs), Amines, Quinone outside Inhibitors (QoIs), Anilinopyrimidines (APs), and Benzimidazoles, as presently defined by the Fungicide Resistance Action Committee (FRAC) Banana Group, and the combination is applied to at least one banana plant. In some embodiments, the fungicidal compound is a demethylation inhibitor (DMI) selected from the group consisting of bitertanol, difenoconazole, epoxiconazole, fenbuconazole, flusilazole, hexaconazole, myclobutanil, propiconazole, tebuconazole, tetraconazole and triadimenol. In some embodiments, the fungicidal compound is a DMI other than bitertanol, difenoconazole, epoxiconazole, fenbuconazole, flusilazole, hexaconazole, myclobutanil, propiconazole, tebuconazole, tetraconazole and triadimenol. In some embodiments, the DMI is selected from imazalil, fenarimol and flutriafol. In some embodiments, the synthetic fungicidal compound is an amine fungicidal compound selected from the group consisting of spiroxamine, fenpropimorph and tridemorph. In some embodiments, the synthetic fungicidal compound is a QoI fungicidal compound selected from the group consisting of azoxystrobin, pyraclostrobin, kesoxym-methyl, picoxystrobin, pyrmetostrobin and trifloxystrobin. In some embodiments, the synthetic fungicidal compound is a strobilurin other than azoxystrobin, pyraclostrobin, kesoxym-methyl, picoxystrobin, pyrmetostrobin and trifloxystrobin. In some embodiments, the synthetic fungicidal compound is pyrimethanil. In some embodiments, the synthetic fungicidal compound is a benzimidazole selected from the group consisting of benomyl, carbendazim, thiabendazole, thiophanate and thiophanate-methyl.

In some embodiments, the synthetic fungicidal compound is a fungicidal compound indicated for the treatment of Black Sigatoka which is selected from the group consisting of mancozeb, chlorothalonil, boscalid and dodine.

In some embodiments, the synthetic fungicidal compound is a compound that is indicated for the treatment of tomato powdery mildew or pepper powdery mildew, and the combination is applied to at least one tomato or pepper plant. In some embodiments, the synthetic fungicidal compound is selected from the group consisting of azoxystrobin, trifloxystrobin, myclobutanil, and triadimenol.

In some embodiments, the synthetic fungicidal compound is indicated for the treatment of carrot *alternaria* and the combination is applied to at least one carrot plant. In some embodiments, the synthetic fungicidal compound is difenoconazole.

In some embodiments, the synthetic fungicidal compound is selected from the group consisting of mancozeb, chlorothalonil, trifloxystrobin, krsoxim-methyl, orysastrobin, fluoxastrobin, azoxystrobin, pyraclostrobin, dimoxystrobin, picoxystrobin, carbendazim, thiophanate-methyl, thiophanate, thiabendazole, benomyl, boscalid, penthiopyrad, thifluzamide, bixafen, fluopyram, isopyrazam, fenpropimorph, fenpropidin, fenarimol, triforine, spiroxamine, tridemorph, elemental sulfur, quinoxyfen, meptyl dinocap, bupirimate, proquinazid, metrafenone, cyflufenamid, tebuconazole, epoxiconazole, propiconazole, prothioconazole, cyproconazole, difenoconazole, metconazole, flusilazole, myclobutanil, flutriafol, triadimefon, penconazole, bitertanol, hexaconazole, triadimenol, tetraconazole, fluquinconazole, triticonazole, fenbuconazole, diniconazole, bromuconazole, ipconazole, simeconazole, imibenconazole, azaconazole, etaconazole and diclobutrazol.

In some embodiments, the treatment is prophylactic treatment. In some embodiments, the treatment is curative.

There is also provided, in accordance with an embodiment of the invention, a kit containing at least one of tea tree oil (TTO) and a synthetic fungicidal compound which is active against a fungus of the class ascomycetes, and instructions that instruct the user how to treat a plant infection caused by a fungus of the class ascomycetes by applying to the plant a combination of a TTO composition and a synthetic fungicidal compound. In some embodiments, the kit contains TTO in a TTO-containing composition. In some embodiments, the kit contains a synthetic fungicidal compound which is active against a fungus of the class ascomycetes. In some embodiments, the instructions instruct to apply the synthetic fungicidal compound at a dosage rate that is less than the rate indicated by the manufacturer as being the correct dosage rate in the absence of a TTO-containing composition. In some embodiments, the instructions instruct to apply the TTO at a dosage rate that is less than the rate indicated by the manufacturer of the TTO as being the correct dosage rate in the absence of a synthetic fungicidal composition. In some embodiments, the instructions instruct to apply the combination simultaneously. In some embodiments, the instructions instruct to apply the combination as a single mixture. In some embodiments, the instructions instruct to apply the combination sequentially. In some embodiments, the instructions instruct to apply the combination as separate compositions. In some embodiments, the instructions instruct to apply the combination in conjunction with at least one of a mineral oil and an emulsifier.

In some embodiments, the instructions instruct to apply the synthetic fungicidal compound at a dosage rate which is not greater than 95% of the correct dosage rate as indicated by the manufacturer in the absence of TTO. In some embodiments, the instructions instruct to apply the synthetic fungicidal compound at a dosage rate at which not greater than 90% of the correct dosage rate as indicated by the manufacturer in the absence of TTO. In some embodiments, the instructions instruct to apply the synthetic fungicidal compound at a dosage rate at which not greater than 85% of the correct dosage rate as indicated by the manufacturer in the absence of TTO. In some embodiments, the instructions instruct to apply the synthetic fungicidal compound at a dosage rate at which not greater than 80% of the correct dosage rate as indicated by the manufacturer in the absence of TTO. In some embodiments, the instructions instruct to apply the synthetic fungicidal compound at a dosage rate at which not greater than 75% of the correct dosage rate as indicated by the manufacturer in the absence of TTO. In some embodiments, the instructions instruct to apply the synthetic fungicidal compound at a dosage rate at which not greater than 70% of the correct dosage rate as indicated by the manufacturer in the absence of TTO. In some embodiments, the instructions instruct to apply the synthetic fungicidal compound at a dosage rate at which not greater than 65% of the correct dosage rate as indicated by the manufacturer in the absence of TTO. In some embodiments, the instructions instruct to apply the synthetic fungicidal compound at a dosage rate at which not greater than 60% of the correct dosage rate as indicated by the manufacturer in the absence of TTO. In some embodiments, the instructions instruct to apply the synthetic fungicidal compound at a dosage rate at which not greater than 55% of the correct dosage rate as indicated by the manufacturer in the absence of TTO. In some embodiments, the instructions instruct to apply the synthetic fungicidal compound at a dosage rate at which not greater than 50% of the correct dosage rate as indicated by the manufacturer in the absence of TTO. In some embodiments, the instructions instruct to apply the synthetic fungicidal compound at a dosage rate at which not greater than 45% of the correct dosage rate as indicated by the manufacturer in the absence of TTO. In some embodiments, the instructions instruct to apply the synthetic fungicidal compound at a dosage rate at which not greater than 40% of the correct dosage rate as indicated by the manufacturer in the absence of TTO. In some embodiments, the instructions instruct to apply the synthetic fungicidal compound at a dosage rate at which not greater than 35% of the correct dosage rate as indicated by the manufacturer in the absence of TTO. In some embodiments, the instructions instruct to apply the synthetic fungicidal compound at a dosage rate at which not greater than 30% of the correct dosage rate as indicated by the manufacturer in the absence of TTO. In some embodiments, the instructions instruct to apply the synthetic fungicidal compound at a dosage rate that is at least 40% of the correct dosage rate as indicated by the manufacturer in the absence of TTO. In some embodiments, the instructions instruct to apply the synthetic fungicidal compound at a dosage rate that is at least 45% of the correct dosage rate as indicated by the manufacturer in the absence of TTO. In some embodiments, the instructions instruct to apply the synthetic fungicidal compound at a dosage rate that is at least 50% of the correct dosage rate as indicated by the manufacturer in the absence of TTO. In some embodiments, the instructions instruct to apply the synthetic fungicidal compound at a dosage rate that is at least 55% of the correct dosage rate as indicated by the manufacturer in the absence of TTO. In some embodiments, the instructions instruct to apply the synthetic fungicidal compound at a dosage rate that is at least 60% of the correct dosage rate as indicated by the manufacturer in the absence of TTO. In some embodiments, the instructions instruct to apply the synthetic fungicidal compound at a dosage rate that is at least 65% of the correct dosage rate as indicated by the manufacturer in the absence of TTO. In some embodiments, the instructions instruct to apply the synthetic fungicidal compound at a dosage rate that is at least 70% of the correct dosage rate as indicated by the manufacturer in the absence of TTO. In some embodiments, the instructions instruct to apply the synthetic fungicidal compound at a dosage rate that is at least 75% of the correct dosage rate as indicated by the manufacturer in the absence of TTO.

In some embodiments, the instructions instruct to apply the TTO-containing composition at a dosage rate that is less than the rate indicated by the manufacturer as the rate used when the TTO-containing composition is applied in the absence of a synthetic fungicidal compound. In some embodiments, the instructions instruct to apply the TTO-containing composition at a dosage rate that is not greater than 95% of the correct dosage rate as indicated by the manufacturer in the absence of application of a synthetic fungicidal compound. In some embodiments, the instructions instruct to apply the TTO-containing composition at a dosage rate that is not greater than 90% of the correct dosage rate as indicated by the manufacturer in the absence of application of a synthetic fungicidal compound. In some embodiments, the instructions instruct to apply the TTO-containing composition at a dosage rate that is not greater than 85% of the correct dosage rate as indicated by the manufacturer in the absence of application of a synthetic fungicidal compound. In some embodiments, the instructions instruct to apply the TTO-containing composition at a dosage rate that is not greater than 80% of the correct dosage rate as indicated by the manufacturer in the absence of application of a synthetic fungicidal compound. In some embodiments, the instructions instruct to apply the TTO-containing composition at a dosage rate that is not greater than 75% of the correct dosage rate as indicated by the manufacturer in the absence of application of a synthetic fungicidal compound. In some embodiments, the instructions instruct to apply the TTO-containing composition at a dosage rate that is not greater than 70% of the correct dosage rate as indicated by the manufacturer in the absence of application of a synthetic fungicidal compound. In some embodiments, the instructions instruct to apply the TTO-containing composition at a dosage rate that is not greater than 65% of the correct dosage rate as indicated by the manufacturer in the absence of application of a synthetic fungicidal compound. In some embodiments, the instructions instruct to apply the TTO-containing composition at a dosage rate that is not greater than 60% of the correct dosage rate as indicated by the manufacturer in the absence of application of a synthetic fungicidal compound. In some embodiments, the instructions instruct to apply the TTO-containing composition at a dosage rate that is not greater than 55% of the correct dosage rate as indicated by the manufacturer in the absence of application of a synthetic fungicidal compound. In some embodiments, the instructions instruct to apply the TTO-containing composition at a dosage rate that is not greater than 50% of the correct dosage rate as indicated by the manufacturer in the absence of application of a synthetic fungicidal compound. In some embodiments, the instructions instruct to apply the TTO-containing composition at a dosage rate that is not greater than 45% of the correct dosage rate as indicated by the manufacturer in the absence of application of a synthetic fungicidal compound. In some embodiments, the instructions instruct to apply the TTO-containing composition at a dosage rate that is not greater than 40% of the correct dosage rate as indicated by the manufacturer in the absence of application of a synthetic fungicidal compound. In some embodiments, the instructions instruct to apply the TTO-containing composition at a dosage rate that is not greater than 35% of the correct dosage rate as indicated by the manufacturer in the absence of a synthetic fungicidal compound. In some embodiments, the instructions instruct to apply the TTO-containing composition at a dosage rate that is not greater than 30% of the correct dosage rate as indicated by the manufacturer in the absence of application of a synthetic fungicidal compound. In some embodiments, the instructions instruct to apply the TTO-containing composition at a dosage rate that at least 40% of the correct dosage rate as indicated by the manufacturer in the absence of application of a synthetic fungicidal compound. In some embodiments, the instructions instruct to apply the TTO-containing composition at a dosage rate that at least 45% of the correct dosage rate as indicated by the manufacturer in the absence of application of a synthetic fungicidal compound. In some embodiments, the instructions instruct to apply the TTO-containing composition at a dosage rate that at least 50% of the correct dosage rate as indicated by the manufacturer in the absence of application of a synthetic fungicidal compound. In some embodiments, the instructions instruct to apply the TTO-containing composition at a dosage rate that at least 55% of the correct dosage rate as indicated by the manufacturer in the absence of application of a synthetic fungicidal compound. In some embodiments, the instructions instruct to apply the TTO-containing composition at a dosage rate that at least 60% of the correct dosage rate as indicated by the manufacturer in the absence of application of a synthetic fungicidal compound. In some embodiments, the instructions instruct to apply the TTO-containing composition at a dosage rate that at least 65% of the correct dosage rate as indicated by the manufacturer in the absence of application of a synthetic fungicidal compound. In some embodiments, the instructions instruct to apply the TTO-containing composition at a dosage rate that at least 70% of the correct dosage rate as indicated by the manufacturer in the absence of application of a synthetic fungicidal compound. In some embodiments, the instructions instruct to apply the TTO-containing composition at a dosage rate that at least 75% of the correct dosage rate as indicated by the manufacturer in the absence of application of a synthetic fungicidal compound.

In some embodiments, the synthetic fungicidal compound is selected from the group consisting of demethylation inhibitors (DMIs), Amines, Quinone outside Inhibitors (QoIs), Anilinopyrimidines (APs), Benzimidazoles, Carboxamides and Morpholines.

In some embodiments, the synthetic fungicidal compound is a fungicidal compound indicated for the treatment of Black Sigatoka which is selected from the group consisting of demethylation inhibitors (DMIs), Amines, Quinone outside Inhibitors (QoIs), Anilinopyrimidines (APs), and Benzimidazoles, as presently defined by the Fungicide Resistance Action Committee (FRAC) Banana Group, and the combination is applied to at least one banana plant. In some embodiments, the fungicidal compound is a demethylation inhibitor (DMI) selected from the group consisting of bitertanol, difenoconazole, epoxiconazole, fenbuconazole, flusilazole, hexaconazole, myclobutanil, propiconazole, tebuconazole, tetraconazole and triadimenol. In some embodiments, the fungicidal compound is a DMI other than bitertanol, difenoconazole, epoxiconazole, fenbuconazole, flusilazole, hexaconazole, myclobutanil, propiconazole, tebuconazole, tetraconazole and triadimenol. In some embodiments, the DMI is selected from imazalil, fenarimol and flutriafol. In some embodiments, the synthetic fungicidal compound is an amine fungicidal compound selected from the group consisting of spiroxamine, fenpropimorph and tridemorph. In some embodiments, the synthetic fungicidal compound is a QoI fungicidal compound selected from the group consisting of azoxystrobin, pyraclostrobin, kesoxym-methyl, picoxystrobin, pyrmetostrobin and trifloxystrobin. In some embodiments, the synthetic fungicidal compound is a strobilurin other than azoxystrobin, pyraclostrobin, kesoxym-methyl, picoxystrobin, pyrmetostrobin and trifloxystrobin. In some embodiments, the synthetic fungicidal compound is pyrimethanil. In some embodiments, the synthetic fungicidal compound is a benzimidazole selected from the group consisting of benomyl, carbendazim, thiabendazole, thiophanate and thiophanate-methyl.

In some embodiments, the synthetic fungicidal compound is a fungicidal compound indicated for the treatment of Black Sigatoka which is selected from the group consisting of mancozeb, chlorothalonil, boscalid and dodine.

In some embodiments, the synthetic fungicidal compound is a compound that is indicated for the treatment of tomato powdery mildew or pepper powdery mildew, and the combination is applied to at least one tomato or pepper plant. In some embodiments, the synthetic fungicidal compound is selected from the group consisting of azoxystrobin, trifloxystrobin, myclobutanil, and triadimenol.

In some embodiments, the synthetic fungicidal compound is indicated for the treatment of carrot *alternaria* and the combination is applied to at least one carrot plant. In some embodiments, the synthetic fungicidal compound is difenoconazole.

In some embodiments, the synthetic fungicidal compound is selected from the group consisting of mancozeb, chlorothalonil, trifloxystrobin, krsoxim-methyl, orysastrobin, fluoxastrobin, azoxystrobin, pyraclostrobin, dimoxystrobin, picoxystrobin, carbendazim, thiophanate-methyl, thiophanate, thiabendazole, benomyl, boscalid, penthiopyrad, thifluzamide, bixafen, fluopyram, isopyrazam, fenpropimorph, fenpropidin, fenarimol, triforine, spiroxamine, tridemorph, elemental sulfur, quinoxyfen, meptyl dinocap, bupirimate, proquinazid, metrafenone, cyflufenamid, tebuconazole, epoxiconazole, propiconazole, prothioconazole, cyproconazole, difenoconazole, metconazole, flusilazole, myclobutanil, flutriafol, triadimefon, penconazole, bitertanol, hexaconazole, triadimenol, tetraconazole, fluquinconazole, triticonazole, fenbuconazole, diniconazole, bromuconazole, ipconazole, simeconazole, imibenconazole, azaconazole, etaconazole and diclobutrazol.

In some embodiments, the treatment is prophylactic treatment. In some embodiments, the treatment is curative.

There is also provided, in accordance with an embodiment of the invention, a composition comprising tea tree oil (TTO) and at least one synthetic fungicidal compound that is active against a fungus of the class ascomycetes. In some embodiments, the composition contains both the TTO and the at least one synthetic fungicidal compound at concentrations that allow the composition to be applied to a plant infected with an infection caused by a fungus of the class ascomycetes to treat the infection without at least one of (a) inducing phytoxicity in the plant and (b) violating government regulations. In some embodiments, the composition contains both the TTO and the at least one synthetic fungicidal compound at concentrations that allow the composition to be applied to the leaves of banana plants without at least one of (a) inducing phytoxicity in the plant and (b) violating government regulations, while at the same time treating Black Sigatoka. In some embodiments, the composition contains both the TTO and the at least one synthetic fungicidal compound at concentrations that require the composition to be diluted prior to application to a plant infected with an infection caused by a fungus of the class ascomycetes in order to treat the infection without at least one of (a) inducing phytoxicity in the plant and (b) violating government regulations. In some embodiments, the composition contains both the TTO and the at least one synthetic fungicidal compound at concentrations that require the composition to be diluted prior to application to the leaves of banana plants in order to avoid at least one of (a) inducing phytoxicity in the plant and (b) violating government regulations. In some embodiments, the composition further comprises at least one of a mineral oil and an emulsifier. In some embodiments the emulsifier is an alkali or ammonium salt of a $C_6$-$C_{26}$ fatty acid or a mixture of such salts. In some embodiments, the emulsifier is selected from the group consisting of ethoxylated fatty acids, ethoxylated castor oils, ethoxylated polyglycol ethers, alkoxylates, sorbitan esters, dodecylbenzene sulphonates, and ethoxylated tristyrylphenol phosphates.

In some embodiments, the concentration of the synthetic fungicidal compound is not greater than 95% of the concentration of the synthetic fungicidal compound in fungicidal compositions prepared in accordance with the manufacturer's instructions in the absence of TTO. In some embodiments, the concentration of the synthetic fungicidal compound is not greater than 90% of the concentration of the synthetic fungicidal compound in fungicidal compositions prepared in accordance with the manufacturer's instructions in the absence of TTO. In some embodiments, the concentration of the synthetic fungicidal compound is not greater than 85% of the concentration of the synthetic fungicidal compound in fungicidal compositions prepared in accordance with the manufacturer's instructions in the absence of TTO. In some embodiments, the concentration of the synthetic fungicidal compound is not greater than 80% of the concentration of the synthetic fungicidal compound in fungicidal compositions prepared in accordance with the manufacturer's instructions in the absence of TTO. In some embodiments, the concentration of the synthetic fungicidal compound is not greater than 75% of the concentration of the synthetic fungicidal compound in fungicidal compositions prepared in accordance with the manufacturer's instructions in the absence of TTO. In some embodiments, the concentration of the synthetic fungicidal compound is not greater than 70% of the concentration of the synthetic fungicidal compound in fungicidal compositions prepared in accordance with the manufacturer's instructions in the absence of TTO. In some embodiments, the concentration of the synthetic fungicidal compound is not greater than 65% of the concentration of the synthetic fungicidal compound in fungicidal compositions prepared in accordance with the manufacturer's instructions in the absence of TTO. In some embodiments, the concentration of the synthetic fungicidal compound is not greater than 60% of the concentration of the synthetic fungicidal compound in fungicidal compositions prepared in accordance with the manufacturer's instructions in the absence of TTO. In some embodiments, the concentration of the synthetic fungicidal compound is not greater than 55% of the concentration of the synthetic fungicidal compound in fungicidal compositions prepared in accordance with the manufacturer's instructions in the absence of TTO. In some embodiments, the concentration of the synthetic fungicidal compound is not greater than 50% of the concentration of the synthetic fungicidal compound in fungicidal compositions prepared in accordance with the manufacturer's instructions in the absence of TTO. In some embodiments, the concentration of the synthetic fungicidal compound is not greater than 45% of the concentration of the synthetic fungicidal compound in fungicidal compositions prepared in accordance with the manufacturer's instructions in the absence of TTO. In some embodiments, the concentration of the synthetic fungicidal compound is not greater than 40% of the concentration of the synthetic fungicidal compound in fungicidal compositions prepared in accordance with the manufacturer's instructions in the absence of TTO. In some embodiments, the concentration of the synthetic fungicidal compound is not greater than 35% of the concentration of the synthetic fungicidal compound in fungicidal compositions prepared in accordance with the manufacturer's instructions in the absence of TTO. In some embodiments, the concentration of the synthetic fungicidal compound is not greater than 30% of the concentration of the synthetic fungicidal compound in fungicidal compositions prepared in accordance with the manufacturer's instructions in the absence of TTO. In some embodiments, the concentration of the synthetic fungicidal compound is at least 40% of the concentration of the synthetic fungicidal compound in fungicidal compositions prepared in accordance with the manufacturer's instructions in the absence of TTO. In some embodiments, the concentration of the synthetic fungicidal compound is at least 45% of the concentration of the synthetic fungicidal compound in fungicidal compositions prepared in accordance with the manufacturer's instructions in the absence of TTO. In some embodiments, the concentration of the synthetic fungicidal compound is at least 50% of the concentration of the synthetic fungicidal compound in fungicidal compositions prepared in accordance with the manufacturer's instructions in the absence of TTO. In some embodiments, the concentration of the synthetic fungicidal compound is at least 55% of the concentration of the synthetic fungicidal compound in fungicidal compositions prepared in accordance with the manufacturer's instructions in the absence of TTO. In some embodiments, the concentration of the synthetic fungicidal compound is at least 60% of the concentration of the synthetic fungicidal compound in fungicidal compositions prepared in accordance with the manufacturer's instructions in the absence of TTO. In some embodiments, the concentration of the synthetic fungicidal compound is at least 65% of the concentration of the synthetic fungicidal compound in fungicidal compositions prepared in accordance with the manufacturer's instructions in the absence of TTO. In some embodiments, the concentration of the synthetic fungicidal compound is at least 70% of the concentration of the synthetic fungicidal compound in fungicidal compositions prepared in accordance with the manufacturer's instructions in the absence of TTO. In some embodiments, the concentration of the synthetic fungicidal compound is at least 75% of the concentration of the synthetic fungicidal compound in fungicidal compositions prepared in accordance with the manufacturer's instructions in the absence of TTO.

In some embodiments, the concentration of the TTO is less than the concentration of the TTO in fungicidal compositions prepared in accordance with the manufacturer's instructions in the absence of a synthetic fungicidal compound. In some embodiments, the concentration of the TTO is not greater than 95% of the concentration of the TTO in fungicidal compositions prepared in accordance with the manufacturer's instructions in the absence of a synthetic fungicidal compound. In some embodiments, the concentration of the TTO is not greater than 90% of the concentration of the TTO in fungicidal compositions prepared in accordance with the manufacturer's instructions in the absence of a synthetic fungicidal compound. In some embodiments, the concentration of the TTO is not greater than 85% of the concentration of the TTO in fungicidal compositions prepared in accordance with the manufacturer's instructions in the absence of a synthetic fungicidal compound. In some embodiments, the concentration of the TTO is not greater than 80% of the concentration of the TTO in fungicidal compositions prepared in accordance with the manufacturer's instructions in the absence of a synthetic fungicidal compound. In some embodiments, the concentration of the TTO is not greater than 75% of the concentration of the TTO in fungicidal compositions prepared in accordance with the manufacturer's instructions in the absence of a synthetic fungicidal compound. In some embodiments, the concentration of the TTO is not greater than 70% of the concentration of the TTO in fungicidal compositions prepared in accordance with the manufacturer's instructions in the absence of a synthetic fungicidal compound. In some embodiments, the concentration of the TTO is not greater than 65% of the concentration of the TTO in fungicidal compositions prepared in accordance with the manufacturer's instructions in the absence of a synthetic fungicidal compound. In some embodiments, the concentration of the TTO is not greater than 60% of the concentration of the TTO in fungicidal compositions prepared in accordance with the manufacturer's instructions in the absence of a synthetic fungicidal compound. In some embodiments, the concentration of the TTO is not greater than 55% of the concentration of the TTO in fungicidal compositions prepared in accordance with the manufacturer's instructions in the absence of a synthetic fungicidal compound. In some embodiments, the concentration of the TTO is not greater than 50% of the concentration of the TTO in fungicidal compositions prepared in accordance with the manufacturer's instructions in the absence of a synthetic fungicidal compound. In some embodiments, the concentration of the TTO is not greater than 45% of the concentration of the TTO in fungicidal compositions prepared in accordance with the manufacturer's instructions in the absence of a synthetic fungicidal compound. In some embodiments, the concentration of the TTO is not greater than 40% of the concentration of the TTO in fungicidal compositions prepared in accordance with the manufacturer's instructions in the absence of a synthetic fungicidal compound. In some embodiments, the concentration of the TTO is not greater than 35% of the concentration of the TTO in fungicidal compositions prepared in accordance with the manufacturer's instructions in the absence of a synthetic fungicidal compound. In some embodiments, the concentration of the TTO is not greater than 30% of the concentration of the TTO in fungicidal compositions prepared in accordance with the manufacturer's instructions in the absence of a synthetic fungicidal compound. In some embodiments, the concentration of the TTO is at least 40% of the concentration of the TTO in fungicidal compositions prepared in accordance with the manufacturer's instructions in the absence of a synthetic fungicidal composition. In some embodiments, the concentration of the TTO is at least 45% of the concentration of the TTO in fungicidal compositions prepared in accordance with the manufacturer's instructions in the absence of a synthetic fungicidal composition. In some embodiments, the concentration of the TTO is at least 50% of the concentration of the TTO in fungicidal compositions prepared in accordance with the manufacturer's instructions in the absence of a synthetic fungicidal composition. In some embodiments, the concentration of the TTO is at least 55% of the concentration of the TTO in fungicidal compositions prepared in accordance with the manufacturer's instructions in the absence of a synthetic fungicidal composition. In some embodiments, the concentration of the TTO is at least 60% of the concentration of the TTO in fungicidal compositions prepared in accordance with the manufacturer's instructions in the absence of a synthetic fungicidal composition. In some embodiments, the concentration of the TTO is at least 65% of the concentration of the TTO in fungicidal compositions prepared in accordance with the manufacturer's instructions in the absence of a synthetic fungicidal composition. In some embodiments, the concentration of the TTO is at least 70% of the concentration of the TTO in fungicidal compositions prepared in accordance with the manufacturer's instructions in the absence of a synthetic fungicidal composition. In some embodiments, the concentration of the TTO is at least 75% of the concentration of the TTO in fungicidal compositions prepared in accordance with the manufacturer's instructions in the absence of a synthetic fungicidal composition.

In some embodiments, the synthetic fungicidal compound is selected from the group consisting of demethylation inhibitors (DMIs), Amines, Quinone outside Inhibitors (QoIs), Anilinopyrimidines (APs), Benzimidazoles, Carboxamides and Morpholines. In some embodiments, the synthetic fungicidal compound is a fungicidal compound indicated for the treatment of Black Sigatoka which is selected from the group consisting of demethylation inhibitors (DMIs), Amines, Quinone outside Inhibitors (QoIs), Anilinopyrimidines (APs), and Benzimidazoles, as presently defined by the Fungicide Resistance Action Committee (FRAC) Banana Group. In some embodiments, the fungicidal compound is a demethylation inhibitor selected from the group consisting of bitertanol, difenoconazole, epoxiconazole, fenbuconazole, flusilazole, hexaconazole, myclobutanil, propiconazole, tebuconazole, tetraconazole and triadimenol. In some embodiments, the synthetic fungicidal compound is a DMI other than bitertanol, difenoconazole, epoxiconazole, fenbuconazole, flusilazole, hexaconazole, myclobutanil, propiconazole, tebuconazole, tetraconazole and triadimenol. In some embodiments, the synthetic fungicidal compound is an amine fungicidal compound selected from the group consisting of spiroxamine, fenpropimorph and tridemorph. In some embodiments, the synthetic fungicidal compound is a QoI fungicidal compound selected from the group consisting of azoxystrobin, pyraclostrobin, kesoxym-methyl, picoxystrobin, pyrmetostrobin and trifloxystrobin. In some embodiments, the fungicidal compound is a strobilurin other than azoxystrobin, pyraclostrobin, kesoxym-methyl, picoxystrobin, pyrmetostrobin and trifloxystrobin. In some embodiments, the synthetic fungicidal compound is pyrimethanil. In some embodiments, the synthetic fungicidal compound is a benzimidazole selected from the group consisting of benomyl, carbendazim, thiabendazole, thiophanate and thiophanate-methyl. In some embodiments, the synthetic fungicidal compound is a fungicidal compound indicated for the treatment of Black Sigatoka which is selected from the group consisting of mancozeb, chlorothalonil, boscalid and dodine. In some embodiments, the synthetic fungicidal compound is a compound that is indicated for the treatment of tomato powdery mildew or pepper powdery mildew. In some embodiments, the synthetic fungicidal compound is selected from the group consisting of azoxystrobin, trifloxystrobin, myclobutanil, and triadimenol. In some embodiments, the synthetic fungicidal compound is indicated for the treatment of carrot *alternaria* and the combination is applied to at least one carrot plant. In some some embodiments, the synthetic fungicidal compound is difenoconazole. In some embodiments, the synthetic fungicidal compound is selected from the group consisting of mancozeb, chlorothalonil, trifloxystrobin, krsoxim-methyl, orysastrobin, fluoxastrobin, azoxystrobin, pyraclostrobin, dimoxystrobin, picoxystrobin, carbendazim, thiophanate-methyl, thiophanate, thiabendazole, benomyl, boscalid, penthiopyrad, thifluzamide, bixafen, fluopyram, isopyrazam, fenpropimorph, fenpropidin, fenarimol, triforine, spiroxamine, tridemorph, elemental sulfur, quinoxyfen, meptyl dinocap, bupirimate, proquinazid, metrafenone, cyflufenamid, tebuconazole, epoxiconazole, propiconazole, prothioconazole, cyproconazole, difenoconazole, metconazole, flusilazole, myclobutanil, flutriafol, triadimefon, penconazole, bitertanol, hexaconazole, triadimenol, tetraconazole, fluquinconazole, triticonazole, fenbuconazole, diniconazole, bromuconazole, ipconazole, simeconazole, imibenconazole, azaconazole, etaconazole and diclobutrazol.

There is also provided, in accordance with an embodiment of the invention, a plant or a portion thereof which has been treated in accordance with a method in accordance with an embodiment of the invention. In some embodiments, the plant is selected from the group consisting of banana, carrot, cucumber, and tomato.

There is also provided, in accordance with an embodiment of the invention, a fruit or vegetable having on its skin or its leaves a synthetic fungicidal compound and tea tree oil or residue of tea tree oil. In some embodiments, the fruit or vegetable is selected from the group consisting of banana, carrot, cucumber, and tomato.

DETAILED DESCRIPTION

There are provided in accordance with embodiments of the invention methods and compositions for treating infections in plants caused by fungi of the class ascomycetes. Examples of such fungi are Erysiphales (which includes powdery mildews), Dothiodoales (which includes *cercospora* and *microsphearella*), Pleosporales (which includes *Alternaria* spp., and the *Venturia* fungi, e.g apple scab disease), Capnodiales (which includes *cladosporium*), and Magnoporthales (which includes the *Pyricularia* fungi, e.g. rice blast in rice). Some examples of such infections are Black Sigatoka in banana plants, powdery mildew in tomato plants, powdery mildew in pepper plants, and *alternaria* in carrot plants. In general these methods involve applying to the leaves of the plant a combination of a tea tree oil (TTO) (which optionally may be in the form of a TTO-containing composition) and a synthetic fungicidal compound. While in some embodiments the invention may be practiced by using the synthetic fungicidal compound at its approved dosage level, in accordance with the manufacturer's instructions, in some embodiments the invention may be practiced by using the synthetic fungicidal compound at a dosage level below that indicated by the manufacturer and/or approved by the relevant regulatory authorities and/or indicated by FRAC for use of the compound without TTO.

The inventors have found that use of a combination of TTO and a synthetic fungicidal compound, wherein the latter is used at a dosage level below that indicated by the manufacturer without TTO and/or approved by the relevant regulatory authorities and/or indicated by FRAC for use of the compound without TTO, can be as effective in combating ascomycetes infections, e.g. Black Sigatoka, carrot *alternaria*, tomato powdery mildew, and pepper powdery mildew, as using the synthetic fungicidal compound alone at the approved level or using TTO alone at the level indicated by the manufacturer. Such combined use, which may also elicit synergistic effects, facilitates a reduced chemical load on the plants, and increases their yield per hectare in comparison to currently indicated uses of commercially available synthetic fungicides used to combat ascomycetes infections such as Black Sigatoka. Furthermore, it has been found that, contrary to conventional wisdom (such as is reflected in the FRAC literature), such combined use does not result in an increased likelihood of the development of fungicidal resistance.

In this application, the term "synthetic fungicidal compound" or "synthetic antifungal compound" is used to refer to those antifungal compounds that are synthesized as opposed to occurring as such in nature. Similarly, "TTO" or "tea tree oil" refers to an essential oil, usually but not necessarily obtained from the leaves of *Melaleuca alternifolia, Melaleuca dissitiflora* or *Melaleuca linariifolia* and usually being clear and generally colorless to pale yellow in color, which meets ISO 4730 (2004) ("Oil of *Melaleuca*, Terpinen-4-ol type", available from the ISO at http://www.iso.org/iso/iso_catalogue/catalogue_tc/catalogue_detail.htm?csnumber=37033).

It will also be appreciated that synthetic fungicidal compounds are generally sold not as the pure chemical compound but as part of a composition that contains other ingredients, which is typically called a "formulation". In some cases, the formulation as sold contains two active ingredients, each operating on the target fungus by a different mechanism of action. The formulation is sold with a label or other instructions for use, which in many countries must be approved by a governmental regulatory body. These instructions may instruct the end-user to dilute the formulation in a particular manner, or may instruct the end-user to use the formulation as sold. In either case, the instructions will indicate a minimum dosage to be used for each type of crop with which the formulation is to be used, for example X liters of the formulation (which the manufacturer has provided at a concentration of Q grams of active ingredient per liter and may have indicated should be diluted to W grams of active ingredient/liter before use) per Y hectares of crop, as well as how the formulation should be applied to the crop (e.g. by spraying). The manufacturer, or a trade group like FRAC, will often also indicate a maximum number of applications per growing season. These instructions are given not only to increase the likelihood of efficacy of the fungicide, but also to minimize the likelihood of the development of fungicidal resistance in the treated fungus or fungi. Thus, in the context of this application, when reference is made to "a dosage rate that is less than the rate indicated by the manufacturer as being the correct dosage rate in the absence of TTO" or "the concentration of the synthetic fungicidal compound in fungicidal compositions prepared in accordance with the manufacturer's instructions in the absence of TTO" or the like, it will be understood that this refers to such a minimum dosage, as would be understood by one skilled in the art even if the manufacturer of the particular fungicidal formulation in question did not indicate such a minimum dosage. The same is true regarding TTO and TTO-containing compositions, mutatis mutandis, when reference is made herein to a dosage rate, concentration or the like for TTO or for a TTO-containing a composition that is "indicated by the manufacturer as being the correct" dosage rate or concentration or the like "in the absence of a synthetic fungicidal composition".

It will also be appreciated that as used herein, unless indicated otherwise "treatment" refers to both the prophylactic treatment of plants as well as the curative treatment thereof. It will be appreciated that prophylactic treatment includes both preventing ascomycetes infection as well as delaying the onset of such infection, and that curative treatment includes both suppressing or eradicating existing fungus as well as delaying or preventing the worsening of an existing infection.

As stated, the synthetic fungicidal compound will generally be supplied as a composition with other ingredients, i.e. as a formulation, although practice of embodiments of the invention is not limited to such cases, and, as is known in the art, it is possible to formulate the raw chemical into a composition which can then be further mixed or diluted for use in accordance with embodiments of the invention. For example, if the raw synthetic fungicidal compound is not water soluble or is only sparingly soluble in water, emulsifiable concentrates or emulsions may be prepared by dissolving the synthetic fungicidal compound in an organic solvent optionally containing a wetting or emulsifying agent and then adding the mixture to water which may also contain a wetting or emulsifying agent. Suitable organic solvents include aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers. Suspension concentrates of largely insoluble solids may be prepared by ball or bead milling with a dispersing agent with a suspending agent included to stop the solid settling. By including suitable additives, for example additives for improving the distribution, adhesive power and resistance to rain on treated surfaces, the different compositions can be better adapted for various utilities. Emulsifiable concentrates and suspension concentrates will normally contain surfactants, e.g. a wetting agent, dispersing agent, emulsifying agent or suspending agent. These agents can be cationic, anionic or non-ionic agents. Suitable cationic agents are, for example, quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates). Suitable non-ionic agents are, for example, the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite. Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% to 10%, more often 0.01% to 10%, by weight of active ingredient may be used.

The following is a list of some commercial products that contain synthetic fungicidal compounds that can be used in accordance with embodiments of the invention; each product contains one or more synthetic fungicidal compounds, although not all the products listed are necessarily approved or formulated for use in the treatment of banana plant leaves:

| Fungicidal compound | Commercial product(s) | Manufacturer(s) |
|---|---|---|
| bitertanol | Baycor ®, Baycoral ®, | Bayer Crop Science |
| difenoconazole | Score ®, Bardos ®, Bogard ®, Geyser ®, Plandom ®, Plover ®, Polyscore ®, Purugen ®, Sico ®, Slick ®, Arix ® Armure ®, Eria ®, Taspa ®, Trial ® | Syngenta |
| epoxiconazole | Opal ® soprano | BASF, MAI |
| fenbuconazole | Indar ® | Dow AgroSciences |
| flusilazole | Nustar ® | DuPont |
| hexaconazole | Oscar, Anvil | Syngenta, MAI |
| myclobutanil | Sisthane, Nova | DOW |
| propiconazole | Tilt, Bamper | MAI, Syngenta |
| tebuconazole | Folicur ®, Horizon ®, Elite ®, Matador ® | Bayer |
| tetraconazole | Domark | Isagro |
| triadimenol | Shavit, Baifidan | Bayer, MAI |
| spiroxamine | Impulse | Bayer |
| fenpropimorph | Volley | BASF |
| tridemorph | Calixin | BASF |
| azoxystrobin | Amistar, Bankit, Cuadris | Syngenta |
| pyraclostrobin | Comet, headline | BASF |
| trifloxystrobin | Flint | Bayer |
| pyrimethanil | Mythus, Scala | Bayer, ISK |
| Triadimenol | Bayfidan, Benefit | |
| carbendazim | Bavistin | Bayer |
| thiabendazole | Mertect | Syngenta |
| thiophanate | | Nipon Soda |
| thiophanate-methyl | TopsinM | Nipon Soda |

Similarly, the TTO will generally be supplied in the form of a composition, e.g. an oil-in-water emulsion, such as is described in US Patent Publication No. 2007/0237837 or as available commercially as Timorex Gold®. However, it will be appreciated that, as described e.g. in US Patent Publication No. 2007/0237837, it is possible to formulate TTO into a composition which can then be further mixed or diluted for use in accordance with embodiments of the invention.

Thus, for example, an aqueous solution of an ammonium or alkali metal salt of a $C_{6-26}$ fatty acid (or mixture of such fatty acids) may be prepared by mixing such a fatty acid with an aqueous solution of a base (or a mixture of bases) such as NaOH, KOH, $Na_2CO_3$, $KHCO_3$, and $NH_3$; TTO may then be mixed into this solution. Depending on the proportions of water, TTO, and fatty acid salt, the result will be either a water-in-oil emulsion (if the TTO is the predominant ingredient) or an oil-in-water emulsion (if the water is the predominant ingredient). Alternatively, TTO and a $C_6$-$C_{26}$ fatty acid or mixture of such fatty acids may be mixed together, and an aqueous solution of a base (or a mixture of bases) such as NaOH, KOH, $Na_2CO_3$, $KHCO_3$, and $NH_3$ may be mixed into this mixture. If desired, this mixture may be further diluted by further addition of water. Depending on the proportions of water, TTO, and fatty acid and base, the result will be either a water-in-oil emulsion (if the TTO is the predominant ingredient) or an oil-in-water emulsion (if the water is the predominant ingredient). Other organic ingredients, such as other emulsifiers, co-solvents such as $C_{1-8}$ alcohols (such as methanol, ethanol, propanol, butanol and the like) or petroleum distillates having a suitable carbon chain range and distribution, and additional etheric oils, may be added at any stage of the mixing process. This composition will generally be further diluted in water prior to use, so that the concentration of TTO in the composition that is actually applied to a plant will generally range from about 0.01 wt. % to about 5 wt. %, although in principle the weight percentage of TTO may be somewhat higher, provided it is not so high that it exerts a phytotoxic effect on the plant being treated. Also, in principle it is possible to use other liquids to dilute the composition, e.g. methanol or ethanol, although water is most commonly used; as mentioned, alcohols, e.g. $C_{1-8}$ alcohols such as ethanol, methanol, isopropanol, butanol, and the like, in small amounts, may be also be useful for formulating the material.

The fatty acids themselves, which may be utilized in a suitable weight ratio relative to the TTO, as is known in the art (see e.g. US 2007/0237837 or WO 2004/021792), may be saturated or unsaturated and straight- or branched-chain. Examples of such are myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid; caproic acid (hexanoic acid), enanthic acid (heptanoic acid), caprylic acid (octanoic acid), pelargonic acid (nonanoic acid), capric acid (decanoic acid), undecylic acid (undecanoic acid), lauric acid (dodecanoic acid), tridecylic acid (tridecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), nonadecylic acid (nonadecanoic acid), arachidic acid (eicosanoic acid), heneicosylic acid (heneicosanoic acid), behenic acid (docosanoic acid), tricosylic acid (tricosanoic acid), lignoceric acid (tetracosanoic acid), pentacosylic acid (pentacosanoic acid) and cerotic acid (hexacosanoic acid). Other emulsifiers which may additionally or alternatively be incorporated into the compositions prior to further dilution with water include, for example, ethoxylated fatty acids, ethoxylated castor oils, sorbitans ester, dodecylbenzene sulphonates, and ethoxylated tristyrylphenol phosphates; as will be appreciated by those skilled in the art, these emulsifiers are generally synthetic emulsifiers. Other examples of suitable emulsifiers (some of which, as will be appreciated by persons skilled in the art, are also surfactants) are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors, methylcellulose, nonyl phenol ethoxylates (such as nonylphenol polyglycol ether with 4 to 30 EO), octyl phenol ethoxylates (such as iso-octylphenol polyglycol ether with EO), tributyl phenol ethoxylates (such as tri-sec-butylphenol polyglycol ether with 4 to 50 EO), tristyrylphenol phosphate (TSP) ethoxylates (such as 2,4,6-tri-(1-phenylethyl)-phenol polyglycol ether with 20 EO), castor oil ethoxylates (such as castor oil ethoxylate with 6 to 54 EO), alkoxylates (such as fatty alcohol block polyalkoxylate with EO), fatty alcohol ethoxylates (such as unsaturated fatty alcohol polyglycol ether with 20 to 80 EO), oxo alcohol polyglycol ether with 4 to 11 EO, alkylbenzene sulfonates (such as alkyl benzene sulfonate triethanolamine salt, alkyl benzene sulfonate sodium salt, alkyl benzene sulfonate calcium salt), fatty acid ethoxylate with 6 to 40 EO, and dodecylbenzene sulphonates (such as calcium dodecyl benzene sulfonate); as is known in the art, "EO" refers to the degree of ethoxylation. It will also be appreciated that such emulsifiers, whether synthetic or natural, may be used instead of the fatty acid salts described above. Mineral oils may also be incorporated into the compositions, either prior to, during or after dilution; if prior to application to the plant, the TTO-containing compositions are also mixed with the synthetic fungicidal compound or formulation containing the synthetic fungicidal compound, the mineral oil(s) or emulsifier(s) may also be added at this stage.

Thus, in some embodiments, compositions containing TTO and the synthetic fungicidal compound, respectively, will be mixed together and, if necessary, diluted, for application to one or plants. In other embodiments, the TTO and synthetic fungicidal compound may be formulated together, e.g. by methods known in the art or developed in the future, and packaged with appropriate instructions for the end-user. From the description above it will be apparent that compositions containing both TTO and the synthetic fungicidal compound may be made by first making a composition containing TTO and an emulsifier, and then mixing in the synthetic fungicidal compound. It will also be appreciated that another way to prepare compositions containing both TTO and the synthetic fungicidal compound is to mix the TTO into a formulation that already contains the synthetic fungicidal compound, such as an existing commercial formulation. If such formulation already contains a sufficient amount of a suitable emulsifier, then the TTO may be mixed directly with the formulation; if the formulation does not contain a sufficient amount of a suitable emulsifier, then such an emulsifier may be added prior to or concomitantly with the mixing in of the TTO. The resulting formulation, which contains both TTO and the synthetic fungicidal compound, may then be diluted as necessary prior to application to the plant. Alternatively, the formulation may be diluted prior to the mixing in of the TTO. In some cases, it may be possible to dissolve the raw synthetic fungicidal compound in pure TTO or in a TTO-containing composition, and to then formulate this into a desired emulsion by addition of e.g. water and a suitable surfactant, optionally with one or more of a co-surfactant, co-solvent, and other inert ingredient; the emulsion may be suitable for dilution e.g. by tank mixing or may be sufficiently dilute for use on plants. Additionally, as will be appreciated by those skilled in the art, the TTO-containing compositions, whether or not they also contain a synthetic fungicidal compound, may be formulated with adjuvants, such as organosilicates like Silwet 77, clays, talc, acids (such as acetic acid or hydrochloric acid), fatty acid oils, gelatin, resins, gums, polyoxyethylene glycols, sulfated alcohols, fatty acid esters, alkyl sulfonates, petroleum sulfonates, polyol fatty acid esters, polyethoxylated fatty acid esters, aryl alkyl polyoxyethylene glycols, alkyl amine acetates, alkyl aryl sulfonates, alkyl phosphates, and polyhydric alcohols. Such TTO-containing compositions, whether or not they also contain a synthetic fungicidal compound, may also be formulated with preservatives such as 1,2-benzisothiazolin-3-one, and/or with stabilizers such as resins, polyoxyethylene glycols, and gums (e.g. xanthan gum and gum Arabic).

Example 1

Tega 50 SC (a concentrated suspension containing 50% trifloxystrobin as active ingredient (500 g/l), available from Bayer Cropscience), Sico 250 EC (available from Syngenta, containing 25% difenoconazole (250 g/l) as an emulsifiable concentrate), and Timorex Gold 22.3 EC (a product containing 22.3% tea tree oil (from *Melaleuca alternifolia*) in an emulsifiable concentrate, available from Biomor) were tested alone and in combination, as described below, against Black Sigatoka on Cavendish banana plants growing in Guatemala. At the beginning of the experiments the plants were young, and were planted with a plant density of 1650 plants/hectare. Each treatment was applied to four plants; total spray volume was calculated for 25 liters/hectare. In each case the material was also mixed with Spraytex-M (Texaco), a mineral oil, 4 l/ha, and Adsee, an emulsifier, 0.04 l/ha, before use. Untreated plants were used as a control.

In all cases, when application of fungicide was made, tank mixes were prepared, using a manual liquefier. Each plant was then sprayed with 25 ml of the appropriate mix, using a backpack sprayer equipped with a mist blower. A picture of the plant was taken weekly and an infection index for each plant was recorded on this basis. Five foliar sprays were applied at weeks 33 (the first application), 37' 39' 42, and week 45 of the calendar year (weeks 1, 5, 7, 10 and 13 of the trial. Disease development on plants was evaluated on weekly basis starting from the first week of the trial using the variables of youngest leaf infected and youngest leaf spotted. In addition the total number of leaves on each plant was recorded on the same dates. Analysis of variance (ANOVA) using the Jump GLM procedure was applied to data; the Tukey-Kramer Test was applied to determine whether differences between treatments were significant. The results are shown in the figures.

In FIGS. 1A-1C, 2A-2C and 3A-3C, the numbers adjacent to the line legends indicate the respective concentrations of the ingredients, e.g. in FIG. 1A "Tega 0.4+TG 0.5" means 0.4 g/l Tega and 0.5 g/l Timorex Gold. It will also be appreciated that the concentrations indicated by the manufacturers for application of the respective active ingredients to banana plants are 0.4 g/l for Sico, 0.4 g/l for Tega, and 0.5 g/l for Timorex Gold.

Figure 1B:
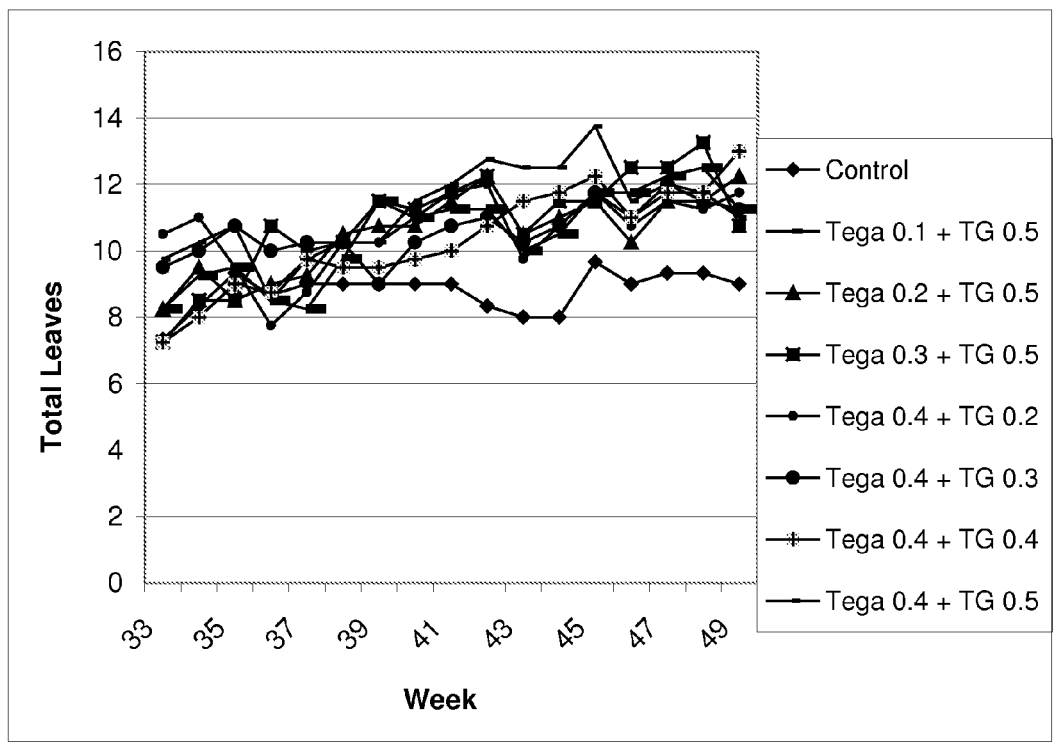
Figure 1C:
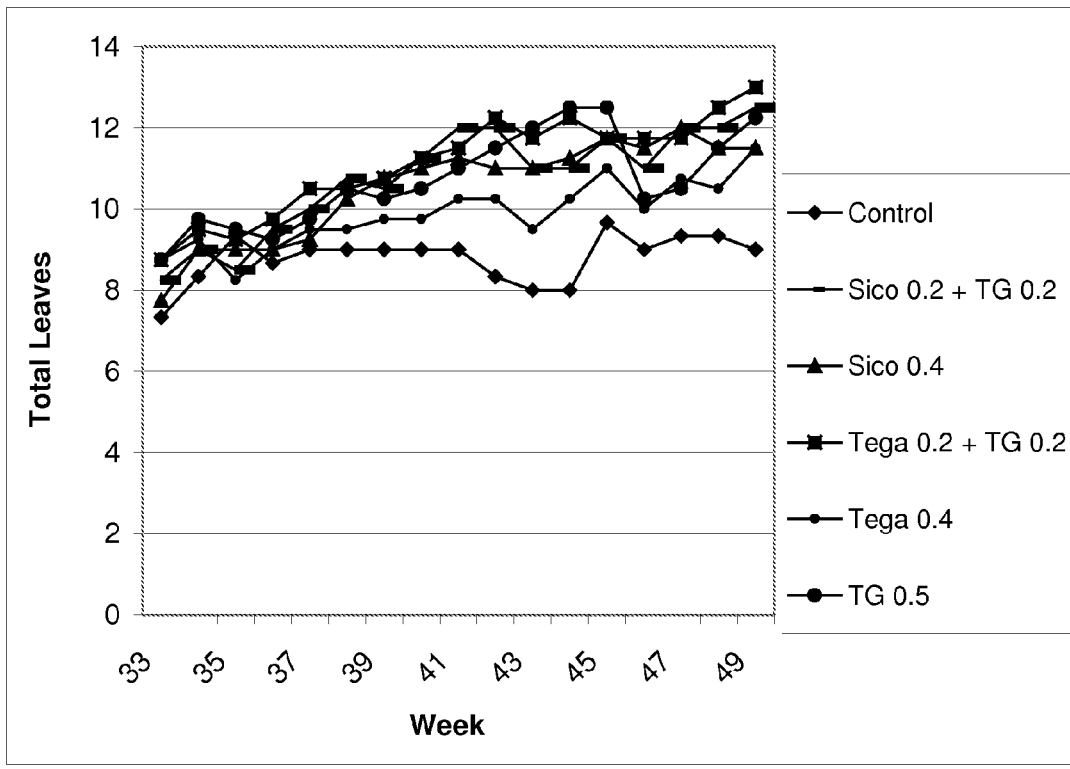

FIGS. 1A-1C show the results for total leaves of the banana plants as a function of time. A larger number of leaves in a banana plant early in its development correlates with a larger yield of bananas—an increase in yield on average of about 10 pounds of banana per hectare of banana plants per additional leaf. It will be noted that in FIGS. 1A-1C, as in FIGS. 2A-2C and 3A-3C, the legends on the graphs refer to week 33, week 34 etc. These are references to the week of the calendar year in which the tests were conducted. Thus "Week 33" on the figure legend denotes week 1 of the trial, "Week 34" on the figure legend denotes week 2 of the trial, etc.

Figure 2A:
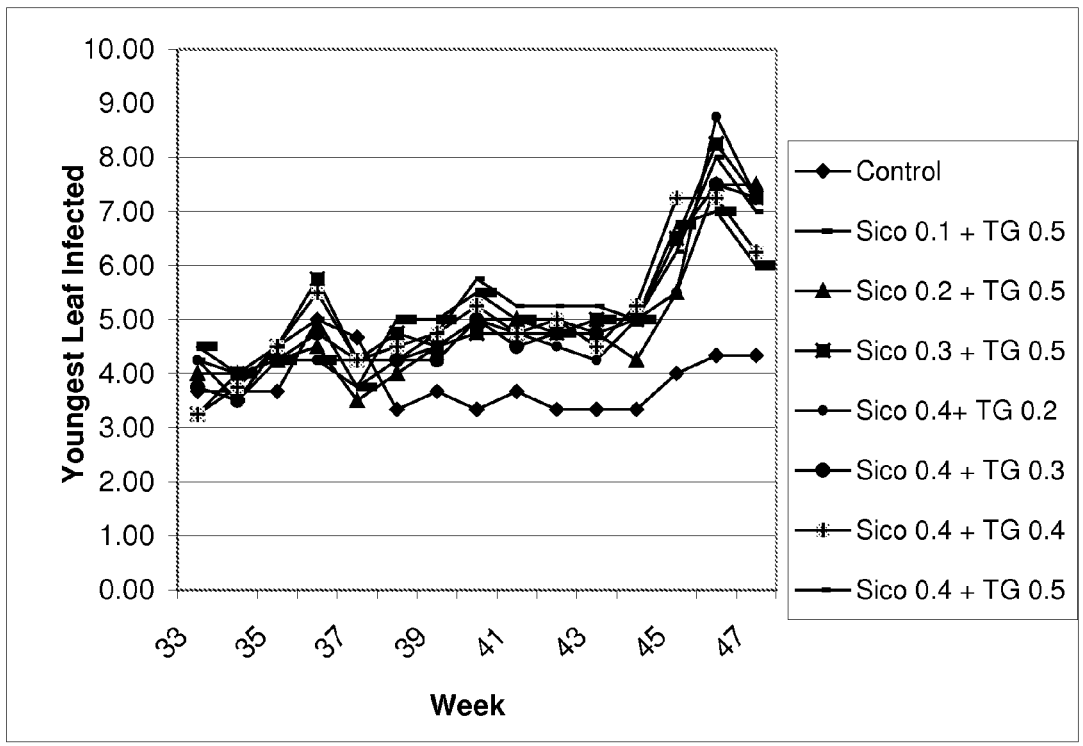
Figure 2B:
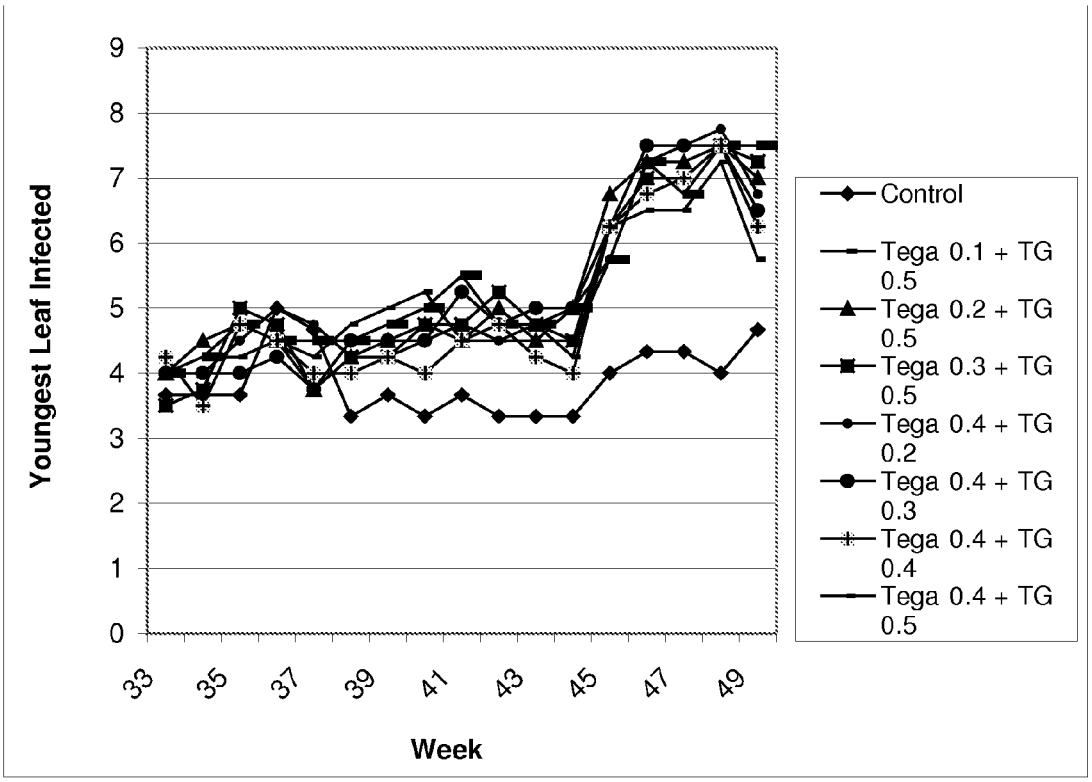
Figure 2C:
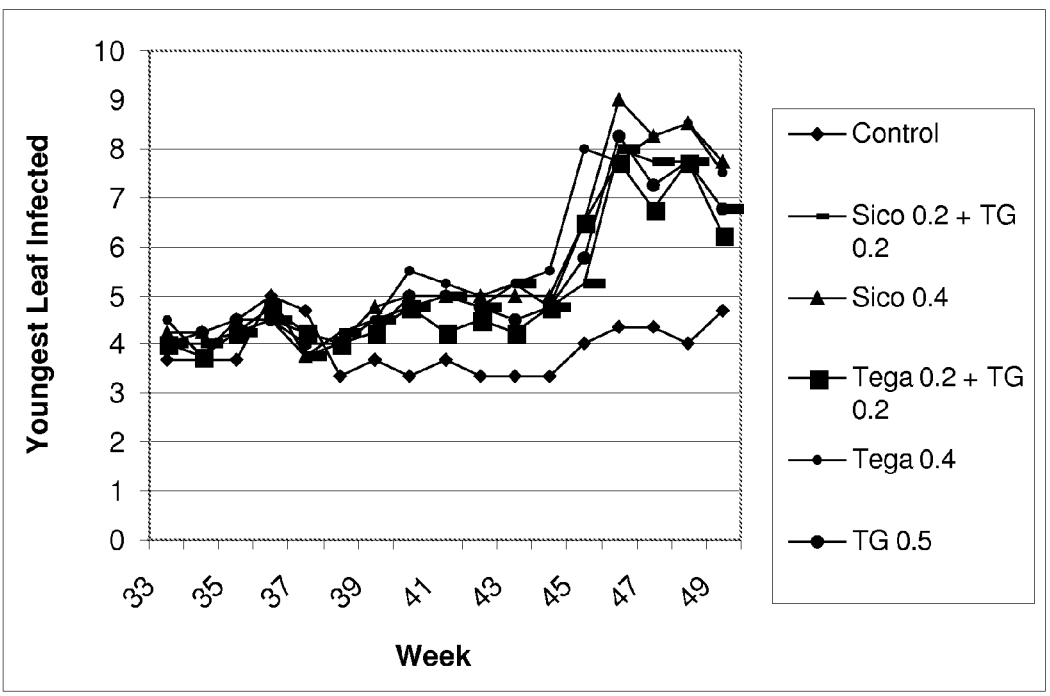

FIGS. 2A-2C show the results for the youngest leaf infection as a function of time. By convention, the youngest leaf in the banana plant, which is found at the top of the plant, is numbered 1, with leaves receive progressively higher numbers the older they are, i.e. the closer they are to the base of the plant. The older the youngest infected leaf, the better the Black Sigatoka fungus has been controlled.

Figure 3A:
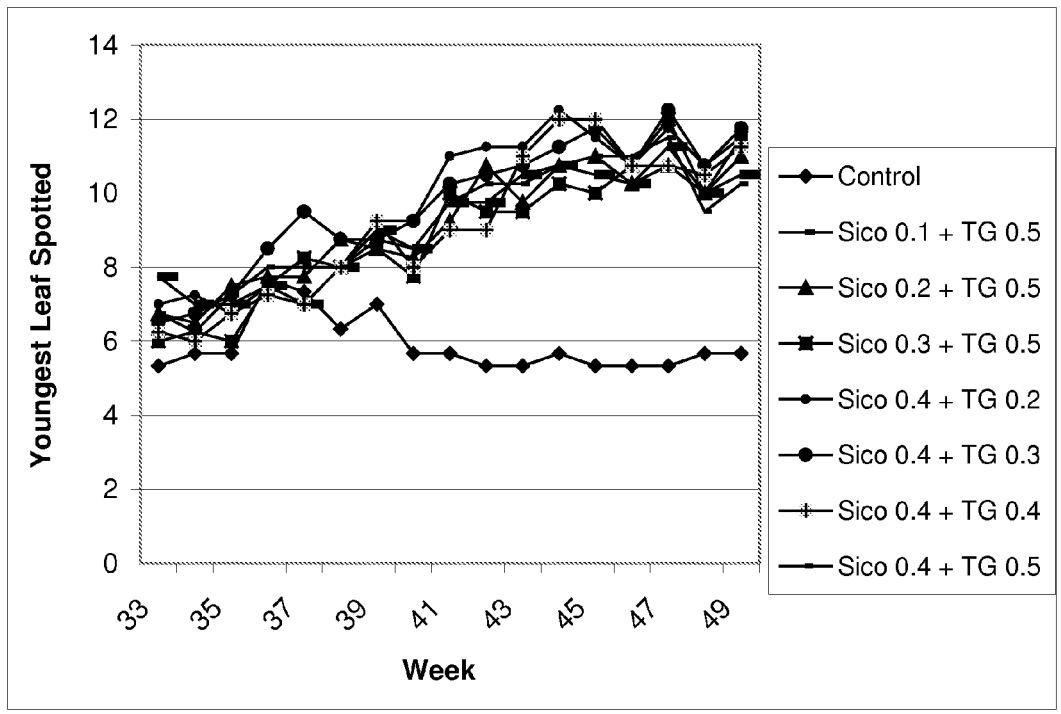
Figure 3B:
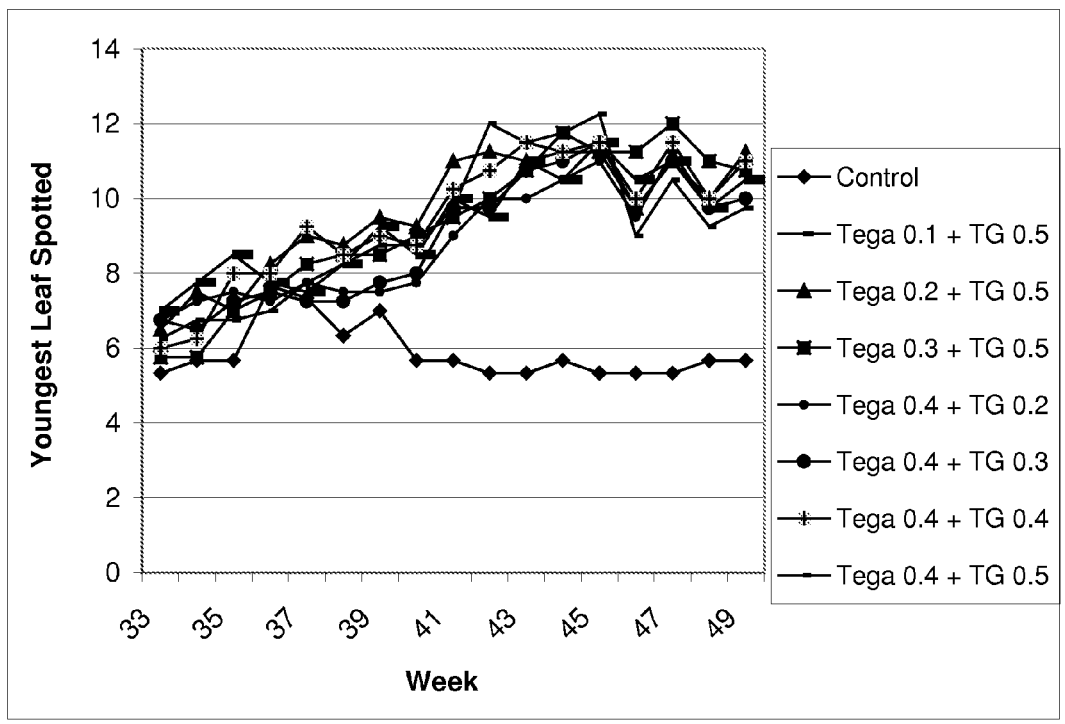
Figure 3C:
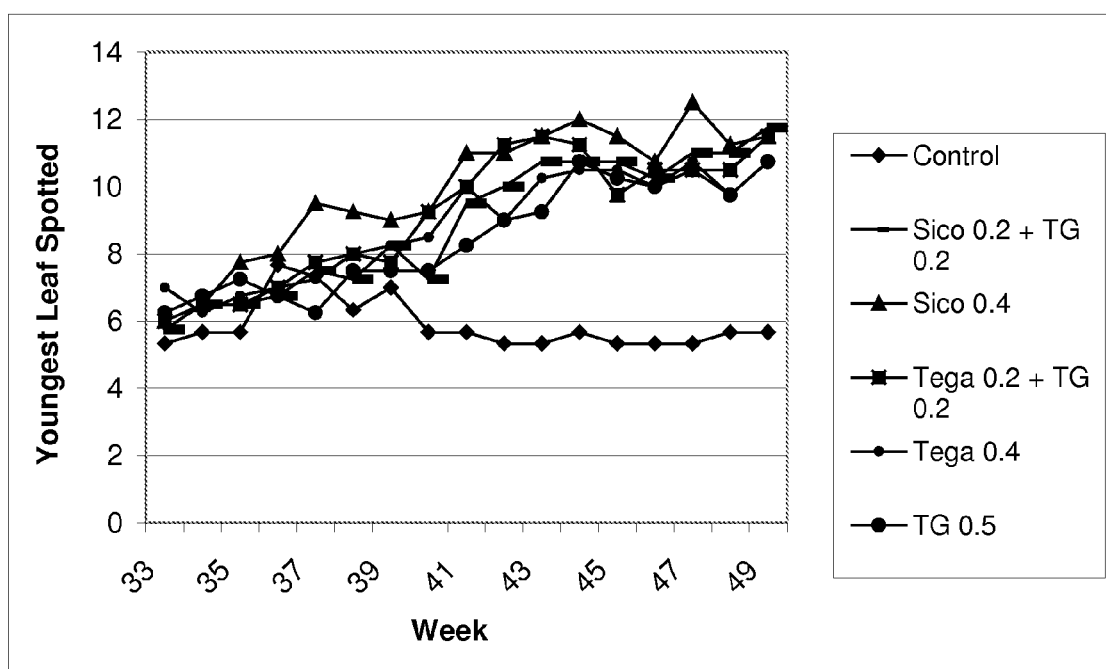

FIGS. 3A-3C show the age of the youngest leaf bearing spots indicative of Black Sigatoka infection. The older the leaf (i.e., the higher the number shown on the Y-axis of the graph), the healthier the plant.

The results show that, contrary to the FRAC Banana Group Guidelines, use of a combination of tea tree oil and a synthetic chemical fungicide can be effective in controlling Black Sigatoka infection, even when the dosage of the synthetic chemical fungicide is less than dosage indicated by the manufacturer as being the proper dosage.

Example 2

The effects of a single application of Timorex Gold alone, Impulse® (spiroxamine) alone, and mixtures of TG and Impulse® on the severity of black sigatoka infestation in banana plants in Costa Rica were evaluated 40, 53 and 60 days after application. The results are shown in the table below; d.a.a.=days after application; numbers are presented as % of disease severity on leaves.

| Treatment | 40 d.a.a. | 53 d.a.a. | 60 d.a.a. |
|---|---|---|---|
| Control | 56.66 | 75 | 80 |
| TG 0.4 l/ha | 11.4 | 19 | 27.3 |
| TG 0.2 l/ha | 14.1 | 29.3 | 50.8 |
| Impulse 0.4 l/ha | 9.2 | 14.77 | 35 |
| Impluse 0.2 l/ha | 21.1 | 40 | 35 |
| TG 0.2 + I 0.2 l/ha | 11.67 | 25 | 41.7 |
| TG 0.4 + I 0.2 l/ha | 15.9 | 29.22 | 43.8 |
| TG 0.2 + I 0.4 l/ha | 12.7 | 25.4 | 39.5 |
| TG 0.4 + I 0.4 l/ha | 11.67 | 10.67 | 19 |

Example 3

Various combinations of TTO (supplied as Timorex Gold®) and synthetic fungicidal compositions (supplied as commercial products to be diluted by the end user prior to use) were tested against tomato powdery mildew and pepper powdery mildew. Open field or greenhouse-grown plants of the crops studied were drip irrigated and fertilized according to known recommendations for each crop. Treatments were applied in a randomized complete block, with 5 replications per treatment. Plot size in each instance was of 5-10 m length, containing 6-20 plants, depending on the crop. Fungicidal treatment was applied using backpack sprayer equipped with a mist blower (STHIL 340) to spray a volume of 600 liter/ha, depending on the crop. From three to eight foliar sprays were applied at 7-14 day intervals, depending on the crop. Disease severity was evaluated by determining the leaf area covered with powdery mildew (disease severity) on each of 20 leaves randomly selected per each replicate. In addition, the incidence of disease was determined by counting the number of leaves exhibiting powdery mildew colonies on each plant. To analyze the results, an arc-sin transformation was performed on the raw data, and analysis of variance (ANOVA) using the SAS GLM procedure was applied to the transformed data. The Tukey-Kramer Test was applied to determine whether differences between treatments were significant. The results are summarized in the tables below. In the tables, "a", "b" and "c", refer to differences in statistical analysis that are familiar to users of the Tukey-Kramer test; "SF" is the "synergy" factor, calculated using the Abbott formula (SF=observed efficacy ($E_{obs}$)/expected efficacy ($E_{exp}$), where $E_{exp}=\alpha+\beta-(4/100)$, where $\alpha$ and $\beta$ denote the levels of control afforded by materials $\alpha$ and $\beta$, respectively, alone; see e.g. Levy et al., EPPO Bull. 16, 651-657 (1986)).

| Tomato Powdery Mildew-Site 1 | | | |
|---|---|---|---|
| 12 days from fourth application | | | |
| | % infected leaf area | Efficacy (%) | SF |
| Severity | | | |
| Control | 60 a | | |
| TG 0.3% | 33.3 b | 44.5 | |
| TG 0.5% | 33.5 b | 44.2 | |
| Azoxystrobin 50 cc/dunam | 5 c | 91.7 | |
| TG 0.3% + Azoxystrobin 50 cc/dunam | 0.3 c | 99.5 | 1.04 |
| Incidence | | | |
| Control | 100 a | | |
| TG 0.3% | 96 a | 4.0 | |
| TG 0.5% | 97 a | 3.0 | |
| Azoxystrobin 50 cc/dunam | 45 bc | 55.0 | |
| TG 0.3% + Azoxystrobin 50 cc/dunam | 12 c | 88.0 | 1.55 |

| Pepper Powdery Mildew-Site 1 | | | |
|---|---|---|---|
| 14 days from third application | | | |
| | % infected leaf area | Efficacy (%) | SF |
| Severity | | | |
| Control | 24.4 a | | |
| TG 0.3% | 16.6 ab | 32.0 | |
| Triadimenol 75 cc/dunam | 8.4 ab | 65.6 | |
| Azoxystronin 50 cc/dunam | 2.9 b | 88.1 | |
| Trifloxystrobin 20 cc/dunam | 1.9 b | 92.2 | |
| TG 0.3% + Triadimenol 75 cc/dunam | 1.3 b | 94.7 | 1.24 |
| TG 0.3% + Azoxystronin 50 cc/dunam | 0 b | 100.0 | 1.09 |
| TG 0.3% + Trifloxystrobin 20 cc/dunam | 1 b | 95.9 | 1.01 |
| Incidence | | | |
| Control | 83.7 a | | |
| TG 0.3% | 83.6 a | 0.1 | |
| Triadimenol 75 cc/dunam | 48.7 ab | 41.8 | |
| Azoxystronin 50 cc/dunam | 22.5 bc | 73.1 | |
| Trifloxystrobin 20 cc/dunam | 25 bc | 70.1 | |
| TG 0.3% + Triadimenol 75 cc/dunam | 18.7 bc | 77.7 | 1.85 |
| TG 0.3% + Azoxystronin 50 cc/dunam | 0 c | 100.0 | 1.37 |
| TG 0.3% + Trifloxystrobin 20 cc/dunam | 16.2 bc | 80.6 | 1.15 |

Pepper Powdery Mildew-Site 2
15 days from ninth application

| | % infected leaf area | Efficacy (%) | SF |
|---|---|---|---|
| Severity | | | |
| Control | 24.4 a | | |
| Trifloxystrobin 20 gr/dunam | 0.1 b | 99.6 | |
| Myclobutanil 60 gr/dunam | 0 b | 100.0 | |
| TG 0.3% | 1.6 b | 93.4 | |
| TG 0.3% + Trifloxystrobin 20 gr/dunam | 0.2 b | 99.2 | 0.99 |
| TG 0.3 + Myclobutanil 60 gr/dunam | 0 b | 100.0 | 1.00 |
| Incidence | | | |
| Control | 64 a | | |
| Trifloxystrobin 20 gr/dunam | 2 b | 96.9 | |
| Myclobutanil 60 gr/dunam | 2 b | 96.9 | |
| TG 0.3% | 28 b | 56.3 | |
| TG 0.3% + Trifloxystrobin 20 gr/dunam | 4 b | 93.8 | 0.95 |
| TG 0.3 + Myclobutanil 60 gr/dunam | 0 b | 100.0 | 1.01 |

Pepper Powdery Mildew-Greenhouse Incidence
23 days from ninth application

| | % leaves infected | Efficacy (%) | SF |
|---|---|---|---|
| Control | 45.67 | | |
| TG 0.5% | 28.20 | 38.25 | |
| TG 0.3% | 33.33 | 27.01 | |
| Flint (trifloxystrobin) 0.02% | 11.33 | 75.18 | |
| TG 0.5% + Flint 0.02% | 0.33 | 99.27 | 1.17 |
| TG 0.3% + Flint 0.02% | 0.33 | 99.27 | 1.21 |

Example 4

Field-grown Nairobi carrot plants were grown according to known recommendations for this crop. Treatments were applied in a randomized complete block, with 5 replications per treatment (240 plants per plot, 4 rows per plot). Fungicidal treatment was applied using a backpack sprayer equipped with a mist blower (STHIL 340). Plants were sprayed on days 1, 13, 26, 41 and 56 of the trial, using the following: Timorex Gold, 0.3%; Amistar® (azoxystrobin), 75% of the recommended dose; Amistar®, 100% of the recommended dose; Score® (difenoconazole), 75% of the recommended dose; Score®, 100% of the recommended dose; and mixtures of 0.3% Timorex Gold with each of 75% and 100% of the recommended dose of each of Amistar® and Score®. 500-750 liters of the spray were applied per hactar. Plants were evaluated on days 19, 26, 40 and 52 for disease severity. Statistics and calculation of the Abbott synergy factor were carried out as described above.

Disease severity was evaluated by determining the leaf area covered with powdery mildew (disease severity) on each of 20 leaves randomly selected per each replicate.

Disease severity (%) on Carrot plants

| Treatment | First Evaluation | Second Evaluation | Third Evaluation | Fourth Evaluation | SF |
|---|---|---|---|---|---|
| Control | 6.1 | 8.5 | 14.1 | 22.0 | |
| TG 0.3% | 7.4 | 8.3 | 13.3 | 18.7 | |
| Amistar 75% | 4.9 | 7.8 | 11.5 | 16.7 | |
| Amistar 100% | 3.7 | 7.9 | 10.5 | 14.0 | |
| TG 0.3 + Amistar 75% | 3.3 | 5.7 | 10.5 | 12.7 | 1.19 |
| TG 0.3% + Amistar 100% | 3.3 | 6.6 | 9.8 | 10.3 | 1.16 |
| Score 75% | 4.1 | 5.2 | 8.7 | 11.7 | |
| Score 100% | 3.7 | 6.9 | 8.3 | 13.0 | |
| TG 0.3 + Score 75% | 5.1 | 8.9 | 11.7 | 13.3 | 0.72 |
| TG 0.3% + Score 100% | 4.5 | 6.4 | 7.9 | 10.5 | 1.05 |

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the general combination of parts that perform the same functions as exemplified in the embodiments, and includes both combinations and subcombinations of the various features described hereinabove as well as variations and modifications thereof, which would occur to persons skilled in the art upon reading the foregoing description.

What is claimed is:

1. A method for treating a plant infection caused by a fungus of the class ascomycetes comprising applying to the plant a combination of tea tree oil (TTO) and a synthetic fungicidal compound selected from the group consisting of demethylation inhibitors (DMIs) that are triazole-based compounds, Quinone outside Inhibitors (QoIs) that are strobilurin-based compounds and spiroxamine, wherein said combination elicits a synergistic effect, and wherein said synergistic effect is determined as a synergy factor (SF) greater than 1, the SF being determined by the equation:

$$SF = \text{observed efficacy}(E_{obs})/\text{expected efficacy}(E_{exp}),$$

where said expected efficacy is $\alpha+\beta-(\alpha\beta/100)$, where $\alpha$ denotes the level of control afforded by the TTO composition, and $\beta$ denotes the level of control afforded by said synthetic fungicidal compound.

2. The method according to claim 1, wherein the combination is applied to the leaves of the plant.

3. The method according to claim 1, wherein the TTO is applied as a TTO-containing composition.

4. The method of claim 3, wherein the TTO is present in the TTO-containing composition in an amount of from 0.01 wt % to 10 wt %.

5. The method of claim 4, wherein the TTO is present in the TTO-containing composition in an amount of not more than 5 wt %.

6. The method of claim 4, wherein the TTO is present in the TTO-containing composition in an amount of at least 0.1 wt %.

7. The method according to claim 1, wherein the combination is applied simultaneously.

8. The method according to claim 1, wherein at least one of the following is true: (a) the synthetic fungicidal compound is applied at a dosage rate that is less than the rate indicated by the manufacturer as being the correct dosage rate in the absence of TTO; (b) the TTO is applied at a dosage rate that is less than the rate indicated by the manufacturer as the rate used when the TTO is applied in the absence of a synthetic fungicidal compound.

9. The method according to claim 1, wherein the dosage rate at which the synthetic fungicidal compound is applied is not greater than 50% of the correct dosage rate as indicated by the manufacturer in the absence of TTO.

10. The method of claim 1, wherein the synthetic fungicidal compound is selected from the group consisting of trifloxystrobin, axoxystrobin, spiroxamine, epoxiconazole, difenoconazole, myclobutanil and triadimenol.

11. The method of claim 1, wherein the synthetic fungicidal compound is selected from the group consisting of trifloxystrobin, epoxiconazole and spiroxamine and the plant infection is caused by the fungus of Black Sigatoka.

12. The method of claim 11, wherein the plant infection is caused by the fungus of Black Sigatoka and the plant is Banana plant.

13. The method of claim 1, wherein the synthetic fungicidal compound is selected from the group consisting of trifloxystrobin, difenoconzole, triadimenol, axoxystrobin and myclobutanil and the plant infection is caused by the fungus of powdery mildew.

14. The method of claim 13, wherein the plant infection is caused by the fungus of powdery mildew and the plant is selected from the group consisting of tomato and pepper.

15. The method of claim 1 wherein the fungus is selected from the group consisting of banana plant Black Sigatoka, carrot *alternaria*, tomato powdery mildew and pepper powdery mildew.

* * * * *